(12) United States Patent
Kaneko et al.

(10) Patent No.: US 9,851,342 B2
(45) Date of Patent: Dec. 26, 2017

(54) DETERIORATION ANALYZING METHOD

(71) Applicant: SUMITOMO RUBBER INDUSTRIES, LTD., Kobe-shi, Hyogo (JP)

(72) Inventors: Fusae Kaneko, Kobe (JP); Hiroyuki Kishimoto, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 700 days.

(21) Appl. No.: 14/345,419

(22) PCT Filed: Nov. 2, 2012

(86) PCT No.: PCT/JP2012/078421
§ 371 (c)(1),
(2) Date: Mar. 18, 2014

(87) PCT Pub. No.: WO2013/065809
PCT Pub. Date: May 10, 2013

(65) Prior Publication Data
US 2014/0349407 A1    Nov. 27, 2014

(30) Foreign Application Priority Data

| Nov. 4, 2011 | (JP) | 2011-242600 |
| Nov. 29, 2011 | (JP) | 2011-260894 |
| Dec. 7, 2011 | (JP) | 2011-268277 |

(51) Int. Cl.
*G01N 33/44* (2006.01)
*G01N 23/06* (2006.01)
(Continued)

(52) U.S. Cl.
CPC ......... *G01N 33/445* (2013.01); *G01N 23/063* (2013.01); *G01N 23/2206* (2013.01);
(Continued)

(58) Field of Classification Search
CPC ....... G01N 2223/623; G01N 2223/632; G01N 23/063; G01N 33/445; G01N 2223/085;
(Continued)

(56) References Cited

U.S. PATENT DOCUMENTS

2006/0120508 A1  6/2006  Chen et al.
2013/0226470 A1  8/2013  Kaneko et al.

FOREIGN PATENT DOCUMENTS

CN        1829910 A     9/2006
EP     2 653 858 A1   10/2013
(Continued)

OTHER PUBLICATIONS

Mukherjee et al., "Onset Kinetics of Thermal Degradation of Ultrathin Polyacrylamide Films", Macromolecules, vol. 42, No. 20, 2009, pp. 7889-7896, XP055117946.
(Continued)

*Primary Examiner* — Rebecca M Fritchman
(74) *Attorney, Agent, or Firm* — Birch, Stewart, Kolasch & Birch, LLP

(57) ABSTRACT

The present invention provides a method of deterioration analysis that enables detailed analysis of the deterioration, especially of the surface, of a polymer material containing at least two diene polymers. The present invention relates to a method of deterioration analysis including: irradiating a polymer material containing at least two diene polymers with high intensity x-rays; and measuring x-ray absorption while varying the energy of the x-rays, to analyze the deterioration of each diene polymer.

20 Claims, 16 Drawing Sheets

(51) Int. Cl.
*G01N 23/22* (2006.01)
*G01N 23/227* (2006.01)
*G06F 19/00* (2011.01)

(52) U.S. Cl.
CPC ... *G01N 23/2273* (2013.01); *G01N 2223/041* (2013.01); *G01N 2223/071* (2013.01); *G01N 2223/085* (2013.01); *G01N 2223/203* (2013.01); *G01N 2223/623* (2013.01); *G01N 2223/627* (2013.01); *G01N 2223/632* (2013.01); *G06F 19/70* (2013.01)

(58) Field of Classification Search
CPC ....... G01N 2223/203; G01N 2223/627; G01N 23/2206; G01N 23/20; G06F 19/70
USPC .............................................. 436/85; 702/22
See application file for complete search history.

(56) References Cited

FOREIGN PATENT DOCUMENTS

| | | |
|---|---|---|
| JP | 2000-137008 A | 5/2000 |
| JP | 2004-99738 A | 4/2004 |
| JP | 2012-141278 A | 7/2012 |
| WO | WO 2004/111624 A2 | 12/2004 |
| WO | WO 2012/081278 A1 | 6/2012 |

OTHER PUBLICATIONS

Rubber Chemistry and Technology, vol. 76, No. 4, 2003, pp. 803-811, XP055115896.
Dhez et al., "Calibrated NEXAFS spectra of some common polymers," Journal of Electron Spectroscopy and Related Phenomena, vol. 128, 2003, pp. 85-96.
International Preliminary Report on Patentability, and Translation of Written Opinion of the International Searching Authority, dated May 6, 2014, for International Application No. PCT/JP2012/078421 (Forms PCT/IB/373 and PCT/ISA/237).
Kaneko et al., "Hoshako o Mochiita Gomu no Kagaku Jotai Bunseki (Chemical state analysis of rubber using radiation)," The Society of Rubber Industry, Japan Kenkyu Happyo Koenkai Koen Yoshi, May 30, 2011, p. 39 (2 pages total).
Klein et al., "Systematic Oxidation of Polystyrene by Ultraviolet-Ozone, Characterized by Near-Edge X-ray Absorption Fine Structure and Contact Angle," Langmuir, vol. 24, No. 15, 2008, pp. 8187-8197.
Okajima, "Analysis of Polymer Surfaces Using XAFS," Surface Science, vol. 23, No. 6, 2002, pp. 359-366.
Mitra et al., "Chemical degradation of crosslinked ethylene-propylene-diene rubber in an acidic environment. Part I. Effect on accelerated sulphur crosslinks", Polymer Degradation and Stability, 91, 2006, pp. 69-80.
Winter et al., "The thermal ageing of poly(3,4-ethylenedioxythiophene). An investigation by X-ray absorption and X-ray photoelectron spectroscopy", Chemical Physics, 194, 1995, pp. 207-213.
Coffey et al., "Characterization of the Effects of Soft X-Ray Irradiation on Polymers," Journal of Election Spectroscopy and Related Phenomena, vol. 122, 2002, pp. 65-78, XP055115895.
Ikeda et al., "Study on Vulcanization and Properties of Styrene-Butadiene Rubber by Synchrotron X-ray and Small-Angle Neutron Scattering," Elastomer Toronkai Koen Yoshishu, Dec. 2, 2010, pp. 155-156 (Total 3 pages), along with English abstract.
International Preliminary Report on Patentability, English translation of the Written Opinion of the International Searching Authority and International Search Report (forms PCT/IB/373, PCT/ISA/237 and PCT/ISA/210), dated May 6, 2014, for International Application No. PCT/JP2012/078421.
International Search Report (form PCT/ISA/210), dated Nov. 15, 2011, for International Application No. PCT/JP2011/068139, along with an English translation.
Minota et al., "Styrene-Butadiene Kyojugo Gomu no Karyu ni Kansuru Kenkyu", The Society of Rubber Industry, Japan Kenkyu Happyo Koenkai Koen Yoshi, May 20, 2010, pp. 16 (Total 2 pages).
Richard, et al., "X-Ray Absorption Near Edge Spectroscopy (XANES) Study of Thermostable Polyphenylquinoxaline (PPQ) Polymer Prior to Cu Thin Films Deposition," Journal de Physique IV, vol. 3, No. C7, Nov. 1993, pp. 789-792, XP055115894.
3. X-ray absorption signal detection, Analysis of Surface Electronic Structure on Nano-materials, Cao Lili, Dec. 31, 2010, pp. 178-181.
3.18X ray absorption spectroscopy fine structure spectrum (XAFS) measurement structure, Shi Changxu, Materials Science and Engineering Handbook, vol. I, Chapter 3, Organizational structure chapter, Dec. 31, 2004, pp. 3-93-3-95.
Special 9X ray analysis technology, University physics, vol. II, Wang Xiue, Dec. 31, 2011, pp. 285-295.
Translated Office Action issued in CN Application No. 201280053328.9 dated Jun. 16, 2017.

DETERIORATION ANALYZING METHOD

TECHNICAL FIELD

The present invention relates to a method of deterioration analysis for analyzing a polymer material containing at least two diene polymers to determine the deterioration of each diene polymer. The present invention also relates to a method of deterioration analysis for analyzing the deterioration of a polymer material.

BACKGROUND ART

To analyze changes in the chemical state of polymer materials caused by deterioration, the following methods are commonly employed: infrared spectroscopy (FT-IR), nuclear magnetic resonance (NMR), X-ray photoelectron spectroscopy (XPS), and the like. Though FT-IR or NMR allows detailed analysis of the chemical state, the information obtained is bulk information, and therefore it is difficult to analyze in detail the chemical state after deterioration which starts at a sample surface.

On the other hand, XPS is a surface-sensitive technique and is thus thought to be effective for analysis of changes in chemical state caused by deterioration. However, polymer materials are generally prepared by blending multiple polymers. For example, in cases where a material contains at least two diene polymers, analyzing the deterioration of each rubber component is important. However, it is difficult to determine the degree of deterioration of each rubber component by analyzing the deterioration by XPS.

Specifically, as shown in the results of XPS measurement performed on isoprene (IR) and butadiene (BR) in FIG. 1-1, chemical shifts of peaks do not occur in the XPS measurement even when different polymer species are used. Accordingly, it is difficult to analyze in detail the deterioration of each rubber component in a rubber blend.

Moreover, in diene polymers, since C=C (double bond) is generally considered to be cleaved due to deterioration, it is important to detect that bond. However, the peak of a C=C bond (double bond) and the peak of a C—C bond (single bond) overlap with each other at around 285 eV, and therefore the decrease in C=C bonds cannot be determined. Furthermore, diene polymers are known to be deteriorated by oxygen and ozone. The peak of oxygen deterioration and the peak of ozone deterioration also overlap with each other, and it is thus difficult to analyze them individually.

Meanwhile, to analyze changes in the chemical state of polymer materials, such as sulfur cross-linked diene rubbers, caused by deterioration, the following methods are commonly employed: physical property tests such as swell test, infrared spectroscopy (FT-IR) and the like.

In the swell test, a sample of a cross-linked polymer material is swelled with a low-molecular-weight solvent such as toluene to determine the network chain density. This method allows analysis of the cleavage and the recombination of rubber molecules before and after deterioration. However, since this method focuses on overall changes, it cannot be used to determine, for example, which is more deteriorated in a sulfur cross-linked polymer material, polymers or sulfur crosslinks. Moreover, in the FT-IR technique, functional groups generated by deterioration, such as C=O and OH, can be detected; however, this technique has low sensitivity to a S—S bond, and thus it cannot be used to determine which is deteriorated as in the case mentioned above.

Furthermore, it is considered that, if the degrees of deterioration of polymers and sulfur crosslinks can be determined individually in the analysis of the deterioration of a polymer material, then more effective measures against deterioration can be taken than conventional measures. The conventional methods as mentioned above also cannot analyze the deterioration ratio between polymers and sulfur crosslinks.

Meanwhile, as disclosed in Non-Patent Literatures 1 to 3, x-ray absorption spectra of polymers have been measured. None of literatures including the above literatures, however, teaches that the deterioration of each polymer in a polymer blend can be detected. Moreover, no document teaches that the oxygen deterioration and the ozone deterioration, into which the deterioration is divided, can be analyzed individually. Furthermore, there is no document relating to distinguishing deterioration factors using x-ray absorption spectra, or even relating to performing deterioration analysis by combining x-ray absorption spectra and X-ray photoelectron spectroscopy.

CITATION LIST

Non Patent Literature

Non-Patent Literature 1: O. Dhez, H. Ade, S. G. Urquhart. J. Electron Spectrosc. Relat. Phenom., 2003, 128, 85-96
Non-Patent Literature 2: Robert J. Klein, Daniel A. Fischer, and Joseph L. Lenhart. Langmuir., 2008, 24, 8187-8197
Non-Patent Literature 3: Toshihiro Okajima, Surface Science, 2002, Vol. 23, No. 6, 356-366

SUMMARY OF INVENTION

Technical Problem

The present invention aims to provide a method of deterioration analysis that solves the above problems and enables detailed analysis of the deterioration, especially of the surface, of a polymer material containing at least two diene polymers.

The present invention also aims to provide a method of deterioration analysis that solves the above problems and enables detailed analysis of the deterioration, especially of the surface, of a polymer material containing at least two diene polymers, to analyze each diene polymer individually.

The present invention aims to provide a method of deterioration analysis that solves the above problems and enables determination of the deterioration of a sulfur cross-linked polymer material, and especially the deterioration ratio between polymers and sulfur crosslinks.

Solution to Problem

A first aspect of the present invention relates to a method of deterioration analysis, including: irradiating a polymer material containing at least two diene polymers with high intensity x-rays; and measuring x-ray absorption while varying the energy of the x-rays, to analyze deterioration of each diene polymer.

In the method of the first aspect, the high intensity x-rays preferably have a brilliance of at least $10^{10}$ (photons/s/mrad$^2$/mm$^2$/0.1% bw). Moreover, an energy range scanned with the high intensity x-rays is preferably not greater than 4000 eV.

The method of the first aspect preferably includes: calculating normalization constants $\alpha$ and $\beta$ using Equations 1-1 based on x-ray absorption spectra obtained by scanning over a required range of high intensity x-ray energies around the carbon K-shell absorption edge within the range of 260 to 400 eV; performing waveform separation of the x-ray absorption spectra around the carbon K-shell absorption edge corrected with the normalization constants $\alpha$ and $\beta$ to obtain peaks attributed to $\pi^*$transition at around 285 eV; and determining degree of deterioration of each diene polymer using Equation 1-2 with areas of the obtained peaks:

[Total area of x-ray absorption spectrum over measurement range of sample before deterioration]×$\alpha$=1, and

[Total area of x-ray absorption spectrum over measurement range of sample after deterioration]×$\beta$=1; and (Equations 1-1)

[1−[($\pi^*$peak area of each diene polymer after deterioration)×$\beta$]/[($\pi^*$peak area of each diene polymer before deterioration)×$\alpha$]]×100=Degree (%) of deterioration. (Equation 1-2)

In the method of the first aspect, peak intensities may be used instead of the peak areas.

A second aspect of the present invention relates to a method of deterioration analysis, including: irradiating a polymer material containing at least two diene polymers with high intensity x-rays; and measuring x-ray absorption in a micro area of the polymer material while varying the energy of the x-rays, to analyze deterioration of each diene polymer.

In the method of the second aspect, an energy range scanned with the high intensity x-rays is preferably not greater than 4000 eV.

The method of the second aspect preferably includes: calculating normalization constants $\alpha$ and $\beta$ using Equations 2-1 based on x-ray absorption spectra of each diene polymer obtained by scanning over a required range of high intensity x-ray energies around the carbon K-shell absorption edge within the range of 260 to 400 eV; performing waveform separation of the x-ray absorption spectra around the carbon K-shell absorption edge corrected with the normalization constants $\alpha$ and $\beta$ to obtain peak areas attributed to $\pi^*$transition at around 285 eV; and determining degree of deterioration of each diene polymer using Equation 2-2 with the obtained peak areas:

[Total area of x-ray absorption spectrum of diene polymer $Ai$ in sample before deterioration]×$\alpha_{Ai}$=1, and

[Total area of x-ray absorption spectrum of diene polymer $Ai$ in sample after deterioration]×$\beta_{Ai}$=1, (Equations 2-1)

wherein Ai represents each diene polymer contained in the polymer material; and

[1−[($\pi^*$peak area of diene polymer $Ai$ after deterioration)×$\beta_{Ai}$]/[($\pi^*$peak area of diene polymer $Ai$ before deterioration)×$\alpha_{Ai}$]]×100=Degree (%) of deterioration of diene polymer $Ai$, (Equation 2-2)

wherein Ai represents each diene polymer contained in the polymer material.

In the method (method of analyzing the degree of deterioration), peak intensities may be used instead of the peak areas.

The method of the second aspect preferably includes: performing waveform separation of an x-ray absorption spectrum of each diene polymer around the oxygen K-shell absorption edge obtained by scanning over a range of high intensity x-ray energies of 500 to 600 eV; and calculating contribution rates of oxygen deterioration and ozone deterioration of each diene polymer according to Equations 2-3, wherein the oxygen deterioration corresponds to a peak on the low energy side with a peak top energy in the range of at least 532 eV but lower than 532.7 eV, and the ozone deterioration corresponds to a peak on the high energy side with a peak top energy in the range of at least 532.7 eV but not higher than 534 eV:

[Peak area of oxygen deterioration of diene polymer $Ai$]/[(Peak area of ozone deterioration of diene polymer $Ai$)+(Peak area of oxygen deterioration of diene polymer $Ai$)]×100=Contribution rate (%) of oxygen deterioration of diene polymer $Ai$, and

[Peak area of ozone deterioration of diene polymer $Ai$]/[(Peak area of ozone deterioration of diene polymer $Ai$)+(Peak area of oxygen deterioration of diene polymer $Ai$)]×100=Contribution rate (%) of ozone deterioration of diene polymer $Ai$, (Equations 2-3)

wherein Ai represents each diene polymer contained in the polymer material.

In the method (method of analyzing the contribution rates of oxygen deterioration and ozone deterioration), peak intensities may be used instead of the peak areas.

The method of the second aspect preferably includes: determining a normalization constant $\gamma$ using Equation 2-4 based on an x-ray absorption spectrum of each diene polymer after deterioration around the carbon K-shell absorption edge; and correcting a total area of an x-ray absorption spectrum of each diene polymer around the oxygen K-shell absorption edge using Equation 2-5 with the normalization constant $\gamma$ to determine the amount of oxygen and ozone bonded to each diene polymer:

[Total area of x-ray absorption spectrum of diene polymer $Ai$ around carbon K-shell absorption edge]×$\gamma_{Ai}$=1, (Equation 2-4)

wherein Ai represents each diene polymer contained in the polymer material; and

[Total area of x-ray absorption spectrum of diene polymer $Ai$ around oxygen K-shell absorption edge]×$\gamma_{Ai}$=Amount (index) of oxygen and ozone bonded to diene polymer $Ai$, (Equation 2-5)

wherein Ai represents each diene polymer contained in the polymer material.

A third aspect of the present invention relates to a method of deterioration analysis, including: irradiating a sulfur cross-linked polymer material with x-rays, and measuring x-ray absorption while varying the energy of the x-rays, to determine deterioration of polymers; irradiating the sulfur cross-linked polymer material with constant energy x-rays, and measuring excited and emitted photoelectrons to determine deterioration of sulfur crosslinks; and determining a deterioration ratio between polymers and sulfur crosslinks from the deterioration of polymers and the deterioration of sulfur crosslinks.

In the method of the third aspect, the polymer material used is preferably a sulfur cross-linked polymer material containing at least one diene polymer, or a polymer material formed by combining the at least one diene polymer and at least one resin followed by sulfur cross-linking.

The method of the third aspect preferably includes: calculating normalization constants $\alpha$ and $\beta$ using Equations 3-1 based on x-ray absorption spectra obtained by scanning over a required range of x-ray energies around the carbon K-shell absorption edge within the range of 260 to 400 eV;

performing waveform separation of the x-ray absorption spectra around the carbon K-shell absorption edge corrected with the normalization constants α and β to obtain peak areas attributed to π*transition at around 285 eV; and determining degree (%) of deterioration of polymers using Equation 3-2 with the obtained peak areas:

[Total area of x-ray absorption spectrum over measurement range of sample before deterioration]× α=1, and

[Total area of x-ray absorption spectrum over measurement range of sample after deterioration]× β=1; and     (Equations 3-1)

[1−[(π*peak area after deterioration)×β]/[(π*peak area before deterioration)×α]]×100=Degree (%) of deterioration of polymers.     (Equation 3-2)

The method of the third aspect preferably includes: dispersing the photoelectrons excited and emitted by irradiation with the constant energy x-rays; measuring S2p photoelectron intensity to obtain an x-ray photoelectron spectrum; performing waveform separation of the spectrum to obtain a peak area attributed to sulfur oxides; and determining degree (%) of deterioration of sulfur crosslinks using Equation 3-3 with the obtained peak area:

(S2p peak area attributed to sulfur oxides)/(Total S2p peak area)×100=Degree (%) of deterioration of sulfur crosslinks.     (Equation 3-3)

The method of the third aspect preferably includes: dispersing the photoelectrons excited and emitted by irradiation with the constant energy x-rays; measuring S1s photoelectron intensity to obtain an x-ray photoelectron spectrum; performing waveform separation of the spectrum to obtain a peak area attributed to sulfur oxides; and determining degree (%) of deterioration of sulfur crosslinks using Equation (3-4) with the obtained peak area:

(S1s peak area attributed to sulfur oxides)/(Total S1s peak area)×100=Degree (%) of deterioration of sulfur crosslinks.     (Equation 3-4)

An energy range of the constant energy x-rays used is preferably from 2.5 to 15 keV.

In the method of the third aspect, peak intensities may be used instead of the peak areas.

The method of the third aspect preferably includes calculating a contribution ratio of deterioration of polymers and deterioration of sulfur crosslinks according to Equation 3-5:

[Degree (%) of deterioration of polymers]/[Degree (%) of deterioration of sulfur crosslinks]=Contribution ratio of deterioration of polymers and deterioration of sulfur crosslinks.     (Equation 3-5)

Advantageous Effects of Invention

The first aspect of the present invention provides a method of deterioration analysis, including: irradiating a polymer material containing at least two diene polymers with high intensity x-rays; and measuring x-ray absorption while varying the energy of the x-rays, to analyze the deterioration of each diene polymer. Even though a polymer material containing at least two diene polymers is used, the method can analyze in detail the deterioration, especially of the surface, of each diene polymer. Accordingly, the method allows the analysis of the deterioration of a polymer material containing at least two diene polymers to determine the degree (%) of deterioration of each diene polymer.

The second aspect of the present invention provides a method of deterioration analysis, including: irradiating a polymer material containing at least two diene polymers with high intensity x-rays; and measuring x-ray absorption in a micro area of the polymer material while varying the energy of the x-rays, to analyze the deterioration of each diene polymer. Even though a polymer material containing at least two diene polymers is used, the method can analyze in detail the deterioration, especially of the surface, of each diene polymer. Accordingly, the method allows the analysis of the deterioration of a polymer material containing at least two diene polymers to determine the degree (%) of deterioration of, the contribution rates of oxygen deterioration and ozone deterioration of, and the amount of oxygen and ozone bonded to each diene polymer.

The third aspect of the present invention provides a method of deterioration analysis, including: irradiating a sulfur cross-linked polymer material with x-rays, and measuring x-ray absorption while varying the energy of the x-rays, to determine the deterioration of polymers; irradiating the sulfur cross-linked polymer material with constant energy x-rays, and measuring excited and emitted photoelectrons to determine the deterioration of sulfur crosslinks; and determining a deterioration ratio between polymers and sulfur crosslinks from the deterioration of polymers and the deterioration of sulfur crosslinks. Thus, the method allows the analysis of the deterioration of a sulfur cross-linked polymer material, especially to determine the deterioration ratio between polymers and sulfur crosslinks. Accordingly, the method can be used to determine which, polymers or sulfur crosslinks, are more deteriorated. This makes it possible to take more effective measures against deterioration than conventional measures.

BRIEF DESCRIPTION OF DRAWINGS

FIG. 1-2 is a graph showing the results of NEXAFS measurement of isoprene rubber and butadiene rubber near the carbon K-shell absorption edge.

FIG. 1-3 is a graph showing the results (before normalization) of NEXAFS measurement of the carbon K-shell absorption edge in a new sample and a deteriorated sample after 1-hour ozone deterioration of an isoprene rubber/butadiene rubber blend.

FIG. 1-4 is a graph showing the results (after normalization) of NEXAFS measurement of the carbon K-shell absorption edge in a new sample and a deteriorated sample after 1-hour ozone deterioration of an isoprene rubber/butadiene rubber blend.

FIG. 1-5 is a graph obtained by performing waveform separation on the normalized results of NEXAFS measurement of the carbon K-shell absorption edge in a new sample of an isoprene rubber/butadiene rubber blend.

FIG. 1-6 is a graph obtained by performing waveform separation on the normalized results of NEXAFS measurement of the carbon K-shell absorption edge in a deteriorated sample after 1-hour ozone deterioration of an isoprene rubber/butadiene rubber blend.

FIG. 2-1 is a schematic diagram illustrating measurement regions of a polymer material in a micro XAFS method and a conventional XAFS method.

FIG. 2-2 is an image of a polymer material subjected to an exposure test at the σ peak of the oxygen K shell.

FIG. 2-3 is a graph showing the results (before normalization) of XPEEM measurement of IR at the carbon K-shell absorption edge in a new sample, a deteriorated sample after 7-hour ozone deterioration, and a deteriorated sample after 1-week oxygen deterioration of an IR/SBR rubber blend.

FIG. 2-4 is a graph showing the results (after normalization) of XPEEM measurement of IR at the carbon K-shell absorption edge in a new sample, a deteriorated sample after 7-hour ozone deterioration, and a deteriorated sample after 1-week oxygen deterioration of an IR/SBR rubber blend.

FIG. 2-5 is a graph showing the results of XPEEM measurement of IR at the oxygen K-shell absorption edge in a new sample, a deteriorated sample after 7-hour ozone deterioration, and a deteriorated sample after 1-week oxygen deterioration of an IR/SBR rubber blend.

FIG. 2-6 is a graph showing the results of XPEEM measurement of IR at the oxygen K-shell absorption edge in a deteriorated sample after complex deterioration (oxygen deterioration and ozone deterioration) of an IR/SBR rubber blend.

FIG. 2-7 is a graph showing the results (after normalization) of XPEEM measurement of IR in a deteriorated sample after 7-hour ozone deterioration and a deteriorated sample after 1-hour ozone deterioration of an IR/SBR rubber blend.

FIG. 3-1 is a graph showing the results (before normalization) of NEXAFS measurement of the carbon K-shell absorption edge in a new sample and a deteriorated sample after 7-hour ozone deterioration of a natural rubber/butadiene rubber blend.

FIG. 3-2 is a graph showing the results (after normalization) of NEXAFS measurement of the carbon K-shell absorption edge in a new sample and a deteriorated sample after 7-hour ozone deterioration of butadiene rubber.

FIG. 3-3 is a graph showing the measurement results of S2p (sulfur 2p orbital) x-ray photoelectron spectra of polymer materials, a new sample and a deteriorated sample after 1-week deterioration by heat and oxygen of a natural rubber/butadiene rubber blend.

FIG. 3-4 is a graph showing the measurement results of S1s (sulfur 1s orbital) x-ray photoelectron spectra of polymer materials, a new sample and a deteriorated sample after 1-week deterioration by heat and oxygen of a natural rubber/butadiene rubber blend.

DESCRIPTION OF EMBODIMENTS

Figure 1:
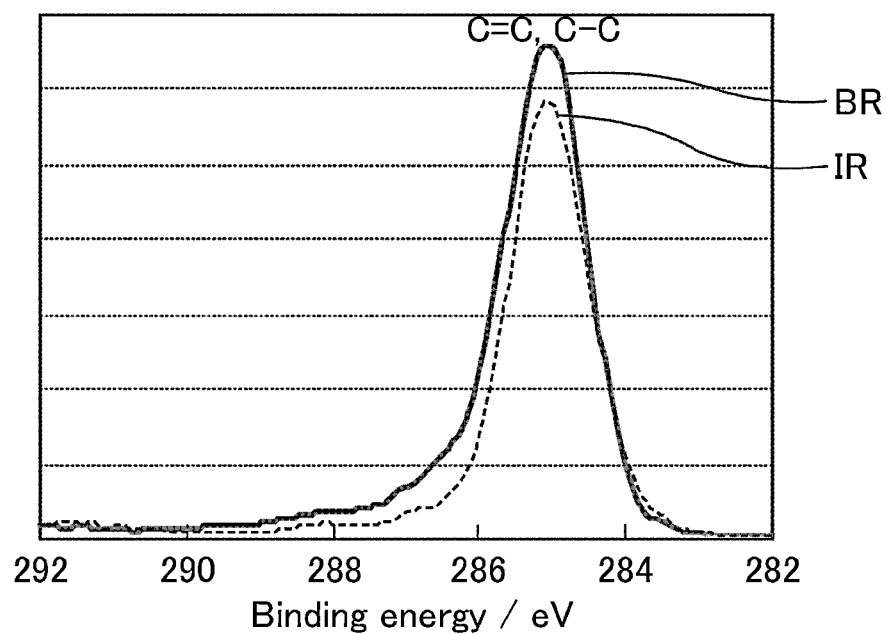
FIG. 1-1 is a graph showing the results of XPS measurement of the carbon 1s orbital in isoprene rubber and butadiene rubber.

The method of deterioration analysis according to the first aspect of the present invention includes: irradiating a polymer material containing at least two diene polymers with high intensity x-rays; and measuring x-ray absorption while varying the energy of the x-rays, to analyze the deterioration of each diene polymer. Known deterioration factors of polymer materials such as rubber include deterioration of polymer molecular chains or cross-linked structures by ultraviolet light, oxygen, ozone, heat, and the like. In order to improve resistance to deterioration, it is important to know what factor is responsible and how the polymer molecular chains or cross-linked structures then change.

In this respect, the first method of deterioration analysis focuses on the use of high intensity x-rays. In this method, new and deteriorated polymer materials containing at least two diene polymers are individually irradiated with high intensity x-rays while the energy of x-rays is varied, to measure x-ray absorption, and then the spectra obtained are compared for each diene polymer, whereby the deterioration of each diene polymer contained in the deteriorated polymer material can be analyzed.

Specifically, a method may be employed which measures an x-ray absorption spectrum near the absorption edge of a specific target element using high intensity x-rays (NEXAFS: Near Edge X-ray Absorption Fine Structure). Since the soft x-ray region includes the absorption edges of light elements, the chemical state of soft materials can be analyzed in detail.

Since x-ray energy is used for scanning in the NEXAFS method, a continuous x-ray generator is needed as the light source. For detailed analysis of the chemical state, an x-ray absorption spectrum with high S/N and S/B ratios needs to be measured. For this reason, a synchrotron is most suitably used in the NEXAFS measurement because it emits x-rays with a brilliance of at least $10^{10}$ (photons/s/mrad$^2$/mm$^2$/0.1% bw) and is a continuous x-ray source. The symbol "bw" indicates a band width of x-rays emitted from a synchrotron.

In the first method of deterioration analysis, the high intensity x-rays preferably have a brilliance (photons/s/mrad$^2$/mm$^2$/0.1% bw) of at least $10^{10}$, more preferably at least $10^{11}$, and still more preferably at least $10^{12}$. The upper limit of the brilliance is not particularly limited, and the X-ray intensity used is preferably low enough not to cause radiation damage.

In the first method of deterioration analysis, the number of photons (photons/s) of the high intensity x-rays is preferably at least $10^7$, and more preferably at least $10^9$. The upper limit of the number of photons is not particularly limited, and the x-ray intensity used is preferably low enough not to cause radiation damage.

In the first method of deterioration analysis, the energy range scanned with the high intensity x-rays is preferably at most 4000 eV, more preferably at most 1500 eV, and still more preferably at most 1000 eV. If the energy range exceeds 4000 eV, the deterioration of a target polymer composite material may not be analyzed. The lower limit is not particularly limited.

The measurement can be performed as follows. For example, a sample placed in an ultrahigh vacuum is irradiated with soft x-rays, so that photoelectrons are emitted. Then electrons flow into the sample from the ground so as to compensate for the emitted photoelectrons, and this current in the sample is measured. Accordingly, such measurement is surface-sensitive but can only measure samples that do not produce gas in vacuo and are electrically conductive. Therefore, in the past, crystals and molecular adsorption have been mainly studied through the measurement, whereas rubber samples that are likely to produce gas and are insulating materials have hardly been studied.

However, the ESCA method, which is similarly surface-sensitive, observes the inner shells of atoms and thus has difficulty in distinguishing the deteriorations of a polymer in detail. In contrast, the NEXAFS method observes atoms and the outer shells that are affected by atoms, and thus allows greater reflection of the impact of elements bonded to a target element than the ESCA method. Therefore, the present inventors have considered that the NEXAFS method can distinguish individual molecular states and thus can distinguish deterioration factors, thereby completing the present invention.

More specifically, the measurement can be conducted by the following method.

A sample mounted on a sample holder is placed in a vacuum chamber for X-ray absorptiometry. Then the sample is irradiated with continuous X-rays that are emitted from a synchrotron and subsequently monochromatized with a monochromator. At that time, secondary electrons and photoelectrons escape from the sample surface into vacuum, and then electrons are replenished from the ground to compensate for the loss of electrons. Then, the X-ray absorption (μL) is calculated using the equation shown below, wherein the X-ray absorption intensity I represents a current flowing from the ground, and the incident X-ray intensity $I_0$ represents a current from a gold mesh provided in an optical system of a beamline (electron yield method). It should be noted that the equation of Lambert-Beer is applicable to the method, and the following equation is thought to hold approximately in the electron yield method:

$I_0(E)/I(E)=\exp(\mu L)\approx\mu L$ ($E$: energy of X-rays, $L$: thickness of sample, $\mu$: absorption coefficient). (Equation)

The following three methods are typically used as the NEXAFS measurement. In examples of the present invention, the electron yield method is employed but is not intended to limit the scope of the invention. Various detection methods may be employed and may be combined for simultaneous measurement.

(Transmission Method)

This is a method of detecting the intensity of the x-rays having passed through a sample. For the measurement of the intensity of transmitted light, for example, a photodiode array detector may be used.

(Fluorescence Method)

This is a method of detecting fluorescent x-rays generated when a sample is irradiated with x-rays. In the case of the transmission method, if the x-ray absorption of an element contained in a small amount in a sample is measured, then a spectrum with a poor S/B ratio is obtained because the signal is small and the background is high due to x-ray absorption by an element contained in a large amount in the sample. In contrast, in the fluorescence method (especially when an energy dispersive detector or the like is used), only the fluorescent x-rays from the target element can be measured and thus the element contained in a large amount has a small influence. Hence, the method is effective to measure an x-ray absorption spectrum of an element contained in a small amount. In addition, since fluorescent x-rays have high penetrating power (low interaction with substances), the fluorescent x-rays generated inside the sample can be detected. Hence, the method is the second most suitable method for obtaining bulk information after the transmission method.

(Electron Yield Method)

This is a method of detecting a current flowing when a sample is irradiated with x-rays. Thus, the sample needs to be an electrically conductive material. Since polymer materials are insulating materials, most of the x-ray absorption measurements of polymer materials have been carried out by putting a very thin layer of a sample on a substrate by deposition, spin-coating or the like. In the present invention, when a polymer material is processed (cut) with a microtome to 100 μm or less, preferably to 10 μm or less, more preferably to 1 μm or less, and still more preferably to 500 nm or less, high S/B and S/N ratios can be achieved through the measurement.

The electron yield method features surface sensitivity (information from the sample surface to a depth of approximately several nanometers). Irradiation of a sample with x-rays causes escape of electrons from elements. Since electrons have a great interaction with substances, their mean free path in a substance is short.

X-ray absorption spectra of a polymer material can be measured by the electron yield method and then analyzed to assay the degree (%) of deterioration. This assay is described below.

For example, the first method of deterioration analysis may include: calculating normalization constants α and β using Equations 1-1 based on x-ray absorption spectra obtained by scanning over a required range of high intensity x-ray energies around the carbon K-shell absorption edge within the range of 260 to 400 eV; performing waveform separation of the x-ray absorption spectra around the carbon K-shell absorption edge corrected with the normalization constants α and β to obtain peaks attributed to π*transition at around 285 eV; and determining the degree of deterioration of each diene polymer using Equation 1-2 with the areas of the obtained peaks:

[Total area of x-ray absorption spectrum over measurement range of sample before deterioration]× α=1, and

[Total area of x-ray absorption spectrum over measurement range of sample after deterioration]× β=1; and (Equations 1-1)

[1−[(π*peak area of each diene polymer after deterioration)×β]/[(π peak area of each diene polymer before deterioration)×α]]×100=Degree (%) of deterioration. (Equation 1-2)

In this manner, the degree (%) of deterioration of each diene polymer after deterioration can be determined to allow analysis of the deterioration rate. In the method of determining the degree of deterioration, the range of high intensity X-ray energies is preferably from 260 to 350 eV. In the method of determining the degree of deterioration, the background is assessed based on a slope before the absorption edge and subtracted, prior to the calculation of Equations 1-1.

In the method of determining the degree of deterioration, each of the total areas of the x-ray absorption spectra in Equations 1-1 is the integral of the spectrum over the measurement range. The energy range can be changed according to the measurement conditions and the like.

The method of determining the degree of deterioration is more specifically described with reference to exemplary measurements of a new sample and a deteriorated sample after 1-hour ozone deterioration of an IR/BR rubber blend.

Figures 1, 2:
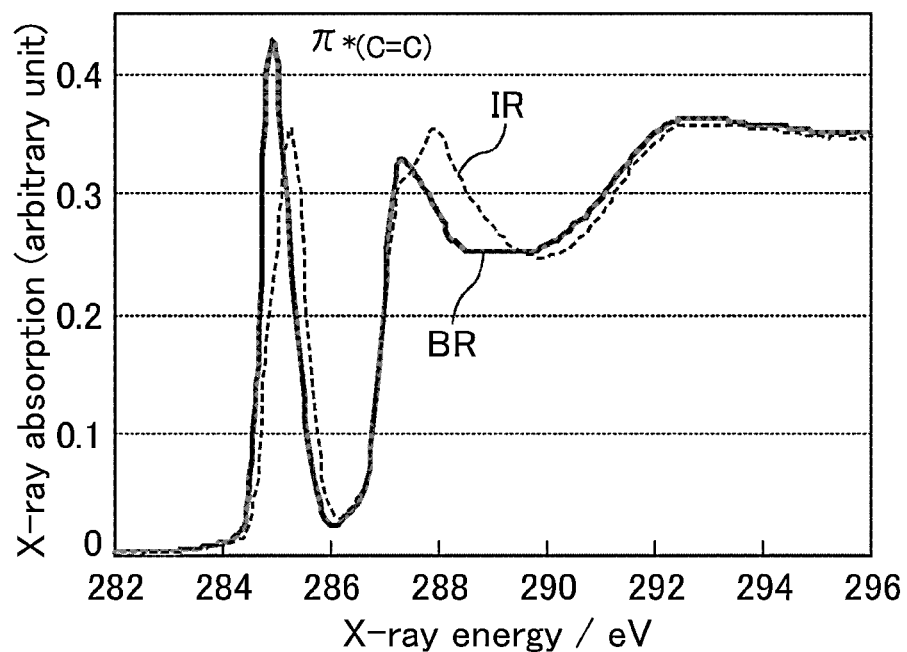

NEXAFS measurement is performed on IR and BR near the carbon K-shell absorption edge in advance. FIG. 1-2 shows the measurement results. Each of IR and BR has a π* transition peak (also referred to as a $\pi^*_{(C=C)}$ peak) attributed to C=C (double bond) at around 285 eV. The peak top energy of IR is about 285.4 eV and the peak top energy of BR is about 284.9 eV, which shows that the peak top energy is different according to the kind of diene polymer (molecular difference).

FIG. 1-2 shows a case of IR and BR as an example. The first aspect of the present invention is applicable regardless of the kind of polymer as long as component polymers in a polymer blend have different peak top energies. For example, since styrene butadiene rubber (SBR) has a peak top energy of about 285.0 eV which is also different from those of IR and BR, the same technique is employable in the case of an SBR rubber blend. Moreover, natural rubber (NR) has the same peak top energy as IR and thus can be treated in the same manner as IR.

Figures 1, 2, 3:
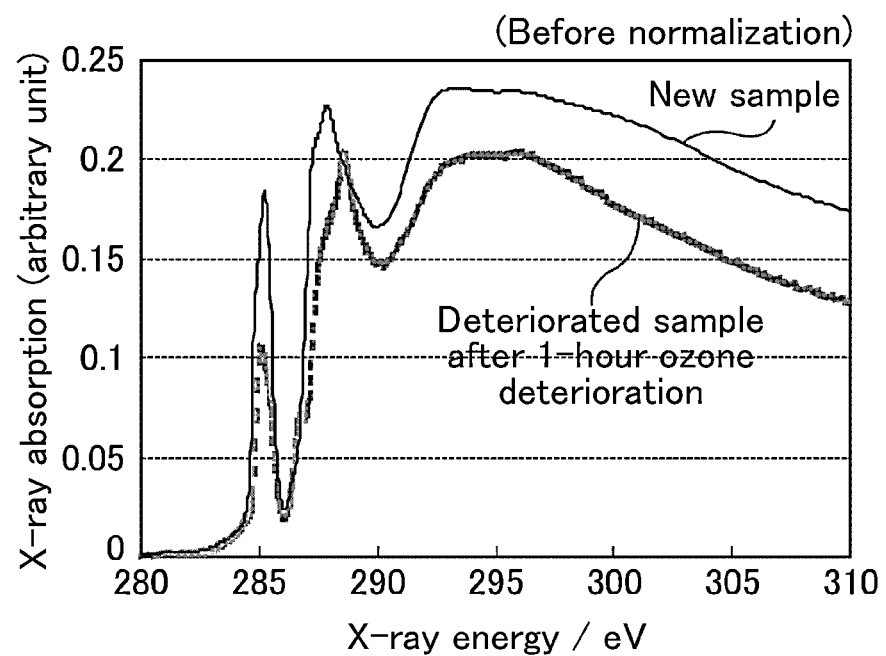

FIG. 1-3 shows the results of NEXAFS measurement of the carbon K-shell absorption edge in a new sample and a deteriorated sample (ozone deterioration). As shown in FIG. 1-3, the deteriorated sample has a smaller π*peak at around 285 eV than the new sample; however, an absolute measurement is difficult to perform by the NEXAFS method because subtle changes in the distance from the light source to the sample and the like affect the magnitude of the X-ray absorption spectrum. For this reason, the results of NEXAFS measurement of the carbon K-shell absorption edge cannot be simply compared between samples.

For comparison between the x-ray absorption spectra of the measured samples, the following normalization is performed (the x-ray absorption spectra of the samples are corrected for direct comparison). Since the amount of X-ray absorption of the shells of carbon does not change before and after deterioration, the area of the carbon K-shell absorption edge peak is normalized to 1 using the Equations 1-1. Specifically, normalization constants $\alpha$ and $\beta$ are first calculated using the Equations 1-1 based on the x-ray absorption spectra before normalization, and then the x-ray absorption spectra before normalization are corrected (normalized) by multiplying the spectra before normalization by $\alpha$ and $\beta$, whereby the $\pi^*$peaks of the samples can be directly compared. FIG. 1-4 shows the thus formed spectra of the carbon K-shell absorption edge after normalization.

For each of new and deteriorated samples, the $\pi^*_{(C=C)}$ peak of the carbon K-shell absorption edge spectrum after normalization in FIG. 1-4 is subjected to waveform separation to obtain a peak attributed to IR with a peak top energy of about 285.4 eV and a peak attributed to BR with a peak top energy of about 284.9 eV. FIGS. 1-5 and 1-6 show spectra of the new and deteriorated samples, respectively, obtained by waveform separation into IR and BR components. The peaks attributed to each polymer component may be separated by waveform separation using a Gaussian function. Or alternatively, a Lorentzian function or an arbitrary function that is a weighted sum of Gaussian and Lorentzian functions may be used.

The degree of deterioration of IR is determined using Equation 1-2 with the peak areas attributed to IR of the new and deteriorated samples shown in FIGS. 1-5 and FIGS. 1-6, respectively. The degree of deterioration of BR is similarly determined using Equation 1-2. The degree of deterioration herein refers to the rate of reduction of a $\pi^*$peak attributed to each diene polymer from before to after deterioration, and means the deterioration rate (%) of each diene polymer contained in a sample.

In the method of determining the degree of deterioration, the degree of deterioration can also be determined by using the peak intensities, instead of the peak areas, in Equation 1-2.

Although the description has been given on the case of an ozone-deteriorated sample, oxygen-deteriorated samples and samples deteriorated by both ozone and oxygen can also be similarly analyzed to determine the degree of deterioration of each polymer component.

The method of the first aspect of the present invention can be carried out using, for example, beamline BL12 at Kyushu Synchrotron Light Research Center in Saga, Japan.

The polymer material usable in the first aspect of the present invention is not particularly limited as long as it contains at least two diene polymers. It may suitably be a rubber blend material containing at least two diene polymers, or a composite material combining the rubber blend material and at least one resin, for example. Examples of the diene polymers include polymers containing double bonds, such as natural rubber (NR), isoprene rubber (IR), butadiene rubber (BR), styrene butadiene rubber (SBR), acrylonitrile butadiene rubber (NBR), chloroprene rubber (CR), butyl rubber (IIR), halogenated butyl rubber (X-IIR), and styrene isoprene butadiene rubber (SIBR).

The resin is not particularly limited and may be, for example, a resin commonly used in the rubber industry field. Examples thereof include petroleum resins such as C5 aliphatic petroleum resins and cyclopentadiene petroleum resins. The method of deterioration analysis of the present invention can be suitably applied to these materials.

As mentioned above, new and deteriorated polymer materials containing multiple diene polymers are irradiated with high intensity x-rays while the energy of high intensity x-rays is varied, and then the degree of deterioration is assayed based on the x-ray absorption. This enables analysis of the deterioration of each diene polymer, as well as the deterioration of the entire sample. Thus, the method of the first aspect of the present invention can be used to analyze the degree of deterioration of each polymer component in commonly used blend materials.

The method of deterioration analysis according to the second aspect of the present invention includes: irradiating a polymer material containing at least two diene polymers with high intensity x-rays; measuring the x-ray absorption in a micro area of the polymer material while varying the energy of the x-rays, to analyze the deterioration of each diene polymer. As mentioned earlier, known deterioration factors of polymer materials such as rubber include deterioration of polymer molecular chains or cross-linked structures by ultraviolet light, oxygen, ozone, heat, and the like. In order to improve resistance to deterioration, it is important to know what factor is responsible and how the polymer molecular chains or cross-linked structures then change.

The present inventors have proposed in Japanese Patent application No. 2011-167131 methods for determining the degree of deterioration of, the contribution rate of oxygen deterioration of, the contribution rate of ozone deterioration of, and the amount of oxygen and ozone bonded to a polymer material by the NEXAFS (Near Edge X-ray Absorption Fine Structure) method in which high intensity x-rays are used to measure x-ray absorption spectra near the absorption edge of a specific element. These methods provide information about a polymer material as a whole; however, in the case of a polymer material including a blend of multiple diene polymers, these methods are incapable of individually analyzing the deterioration of each diene polymer. Although the present inventors have proposed the method of deterioration analysis of the first aspect of the present invention, in which the degree of deterioration of each diene polymer blended in a polymer material is assessed by the NEXAFS method, this method also cannot determine the contribution rates of oxygen deterioration and ozone deterioration and the amount of bonded oxygen and ozone for each diene polymer.

In contrast, in the method of deterioration analysis of the second aspect of the present invention, new and deteriorated polymer materials containing at least two diene polymers are irradiated with high intensity x-rays while the energy of x-rays is varied, to measure the x-ray absorption in a micro area of the polymer materials, and then the resulting spectra are compared for each diene polymer. Thus, the deterioration of each diene polymer in a deteriorated polymer material can be individually analyzed. In other words, in the method of deterioration analysis of the second aspect of the present invention, x-ray absorption spectra are measured for each diene polymer, and these spectra are compared. This enables determination of the contribution rates of oxygen deterioration and ozone deterioration and the amount of bonded oxygen and ozone, in addition to the degree (%) of deterioration, for each diene polymer.

Specifically, a micro XAFS method (X-ray Absorption Fine Structure) may be employed in which high intensity x-rays are used to measure an x-ray absorption spectrum in a micro area of a sample. As shown in FIG. 2-1, conventional XAFS not having a space resolution detects the absorption of the entire sample, whereas the micro XAFS method having a space resolution of typically not more than 100 nm measures the x-ray absorption spectrum in a micro area of a sample. Thus, the micro XAFS can be used to measure an x-ray absorption spectrum for each diene polymer blended in a sample and thereby detect the difference in absorption between diene polymers.

From the standpoint of providing an excellent space resolution, the micro XAFS method is preferably one in which measurement is carried out in a soft x-ray region (micro NEXAFS), and is more preferably x-ray photo emission electron microscopy (XPEEM) or scanning transmission x-ray microscopy (STXM).

In the XPEEM method, a sample is irradiated with high intensity x-rays, and the sample absorbs the x-rays, so that electrons are emitted from the sample surface. The emitted electrons are magnified by an electron lens (electrostatic or magnet type) while maintaining their positions and intensities. Accordingly, as shown in FIG. 2-2, morphology observation of at least two diene polymers blended together can be carried out. Moreover, since the amount of electrons emitted from a sample is proportional to the x-ray absorption coefficient, the difference in absorption between diene polymers can be detected. Thus, the degree of deterioration, the contribution rates of oxygen deterioration and ozone deterioration, and the amount of bonded oxygen and ozone can be determined for each diene polymer using the Equations 2-1 to 2-5.

In the XPEEM method, the photoelectron emission intensity may be determined as a function of the position on the sample surface by irradiating a sample with high intensity x-rays and raster scanning the sample around the x-rays.

In the STXM method, a micro area of a sample is irradiated with high intensity x-rays focused with a Fresnel zone plate, and then a light having passed through the sample (transmitted light) and the incident light are measured to determine the x-ray absorption in the micro area. Thus, the difference in absorption between diene polymers is detectable; therefore, the degree of deterioration, the contribution rates of oxygen deterioration and ozone deterioration, and the amount of bonded oxygen and ozone can be determined for each diene polymer using the Equations 2-1 to 2-5.

The high intensity x-rays may be focused with a Kirkpatrick-Baez (K-B) focusing system, in which an x-ray reflector is used, instead of the Fresnel zone plate.

Since x-ray energy is used for scanning in the XPEEM and STXM methods, a continuous x-ray generator is needed as the light source. For detailed analysis of the chemical state, an x-ray absorption spectrum with high S/N and S/B ratios also needs to be measured. For this reason, a synchrotron is most suitably used in the XPEEM or STXM measurement because it emits x-rays with a brilliance of at least $10^{10}$ (photons/s/mrad$^2$/mm$^2$/0.1% bw) and is a continuous x-ray source. The symbol "bw" indicates a band width of x-rays emitted from a synchrotron.

In the second method of deterioration analysis, the brilliance of the high intensity x-rays, the number of photons of the high intensity x-rays, and the energy range scanned with the high intensity x-rays are preferably as mentioned for the first method of deterioration analysis.

The ESCA method, which is surface-sensitive, observes the inner shells of atoms and thus has difficulty in distinguishing the deteriorations of a polymer in detail. In contrast, the XPEEM and STXM methods observe excitation to an unoccupied orbital, and thus allow greater reflection of the impact of elements bonded to a target element than the ESCA method. Therefore, the present inventors have considered that the XPEEM or STXM method can distinguish individual bonding states and thus can distinguish deterioration factors, thereby completing the second aspect of the present invention.

The micro XAFS method can be used to measure and analyze x-ray absorption spectra of a polymer material and thereby assay the degree (%) of deterioration, the contribution rates (%) of oxygen deterioration and ozone deterioration, and the amount (deterioration indicator) of bonded oxygen and ozone for each blended polymer. This will be explained below.

For example, the second method of deterioration analysis may include: calculating normalization constants $\alpha$ and $\beta$ using Equations 2-1 based on x-ray absorption spectra of each diene polymer obtained by scanning over a required range of high intensity x-ray energies around the carbon K-shell absorption edge within the range of 260 to 400 eV; performing waveform separation of the x-ray absorption spectra around the carbon K-shell absorption edge corrected with the normalization constants $\alpha$ and $\beta$ to obtain peak areas attributed to $\pi^*$transition at around 285 eV; and determining the degree of deterioration of each diene polymer using Equation 2-2 with the obtained peak areas:

[Total area of x-ray absorption spectrum of diene polymer $Ai$ in sample before deterioration]× $\alpha_{Ai}$=1, and

[Total area of x-ray absorption spectrum of diene polymer $Ai$ in sample after deterioration]× $\beta_{Ai}$=1, (Equations 2-1)

wherein Ai represents each diene polymer contained in the polymer material; and

[1−[($\pi^*$peak area of diene polymer $Ai$ after deterioration)×$\beta_{Ai}$]/[($\pi^*$peak area of diene polymer $Ai$ before deterioration)×$\alpha_{Ai}$]]×100=Degree (%) of deterioration of diene polymer $Ai$, (Equation 2-2)

wherein Ai represents each diene polymer contained in the polymer material.

In this manner, the degree (%) of deterioration of each diene polymer after deterioration can be determined to allow analysis of the deterioration rate. In the method of determining the degree of deterioration, the range of high intensity X-ray energies is preferably from 260 to 350 eV. In the method of determining the degree of deterioration, the background is assessed based on a slope before the absorption edge and subtracted, prior to the calculation of Equations 2-1.

In the method of determining the degree of deterioration, each of the total areas of the x-ray absorption spectra in the Equations 2-1 is the integral of the spectrum over the measurement range. The energy range can be changed according to the measurement conditions and the like.

The method of determining the degree of deterioration is more specifically described with reference to exemplary measurements of a new sample, a deteriorated sample after 7-hour ozone deterioration, and a deteriorated sample after 1-week oxygen deterioration of an IR/SBR rubber blend.

FIG. 2-3 shows the XPEEM measurement results of IR near the carbon K-shell absorption edge in a new sample, a deteriorated sample after 7-hour ozone deterioration, and a deteriorated sample after 1-week oxygen deterioration of an IR/SBR rubber blend. As shown in FIG. 2-3, the deteriorated samples have smaller $\pi^*$peaks at around 285 eV than the new sample; however, an absolute measurement is difficult to perform by the XPEEM or STXM method because subtle changes in the distance from the light source to the sample and the like affect the magnitude of the X-ray absorption spectrum. For this reason, the results of XPEEM or STXM measurement of the carbon K-shell absorption edge cannot be simply compared between samples.

For comparison between the x-ray absorption spectra of the measured samples, the following normalization is performed (the x-ray absorption spectra of the samples are corrected for direct comparison). Since the amount of X-ray absorption of the shells of carbon does not change before and after deterioration, the area of the carbon K-shell absorption edge peak is normalized to 1 using the Equations 2-1. Specifically, normalization constants $\alpha$ and $\beta$ are first calculated using the Equations 2-1 based on the x-ray absorption spectra before normalization, and then the x-ray absorption spectra before normalization are corrected (normalized) by multiplying the spectra before normalization by $\alpha$ and $\beta$, whereby the $\pi^*$peaks of the samples can be directly compared.

Figures 1, 2, 3, 4:
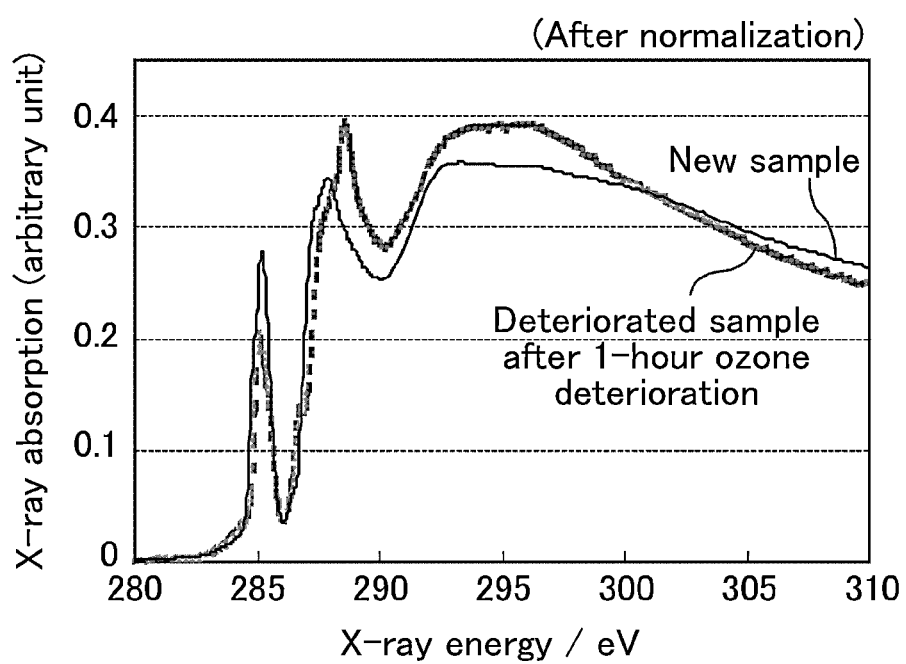
Figures 1, 2, 3, 4, 5:
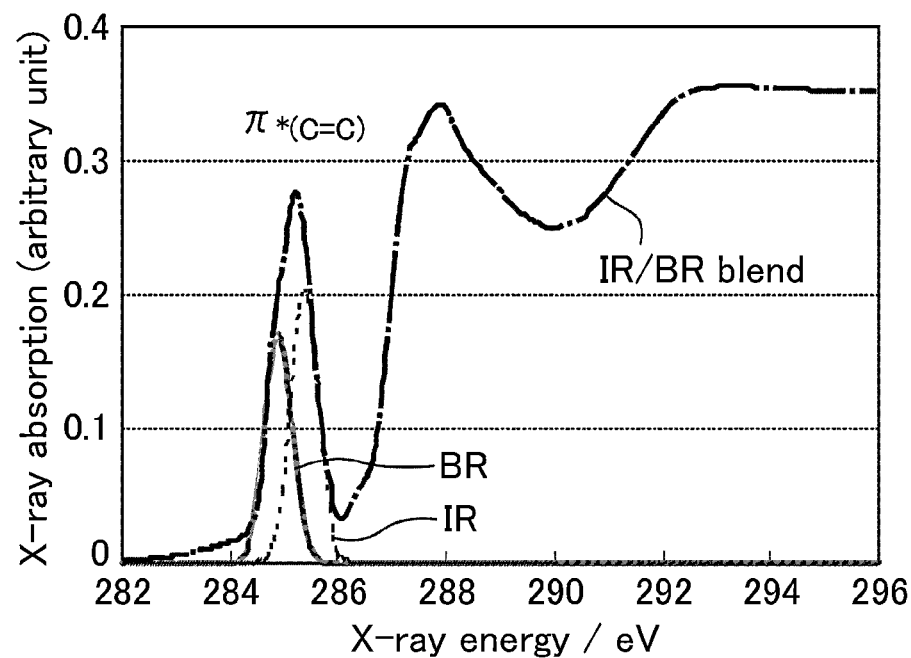
Figures 1, 2, 3, 4, 5, 6:
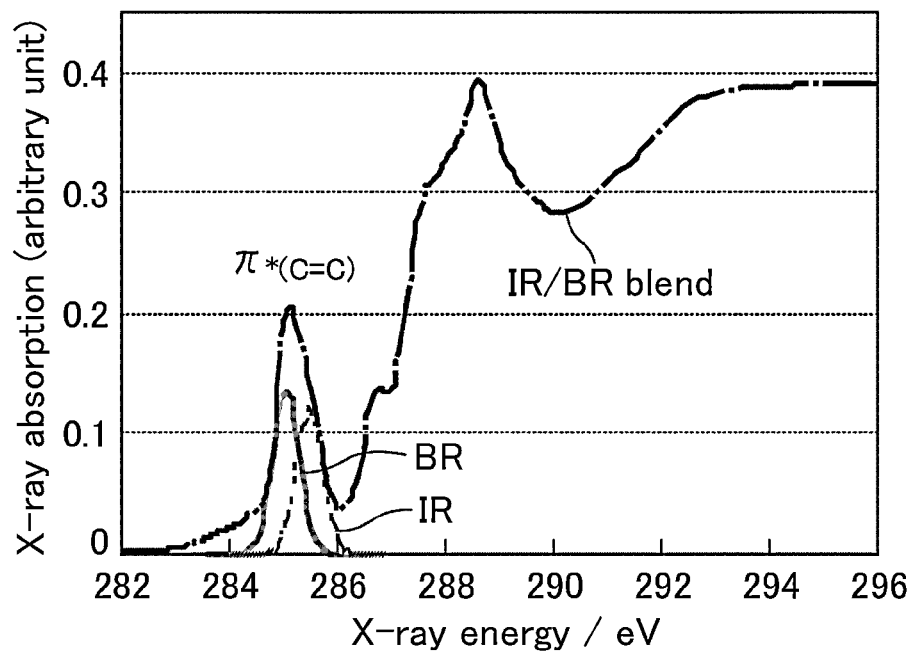
Figures 1, 2:
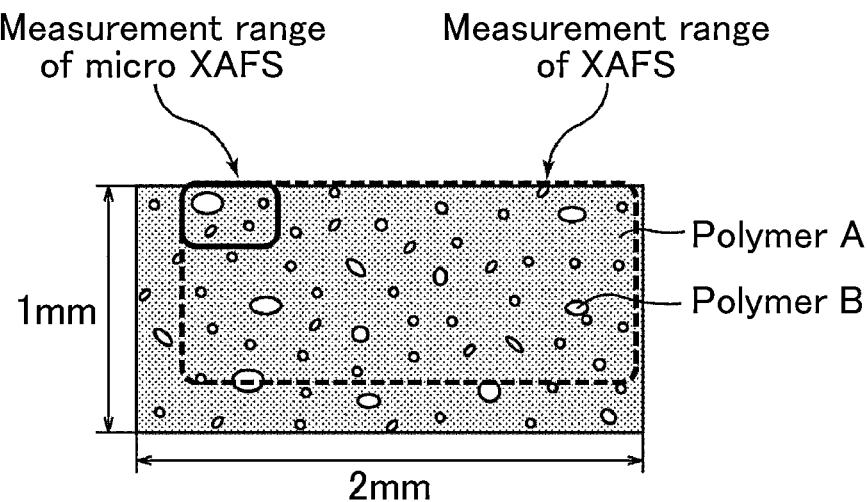
Figure 2:
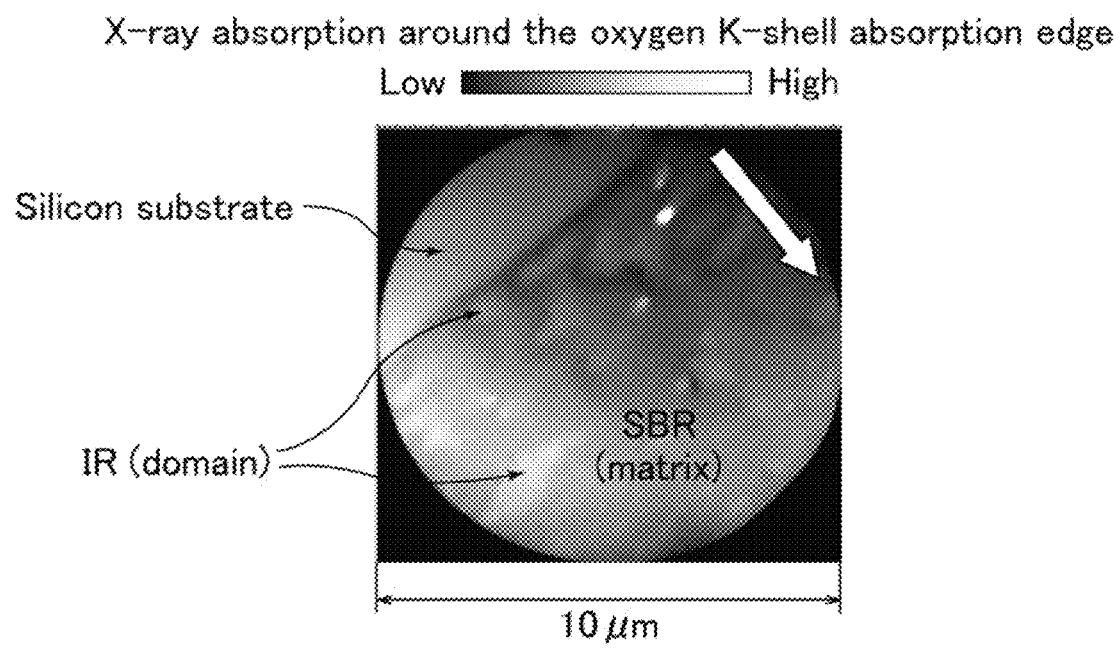
Figures 2, 3:
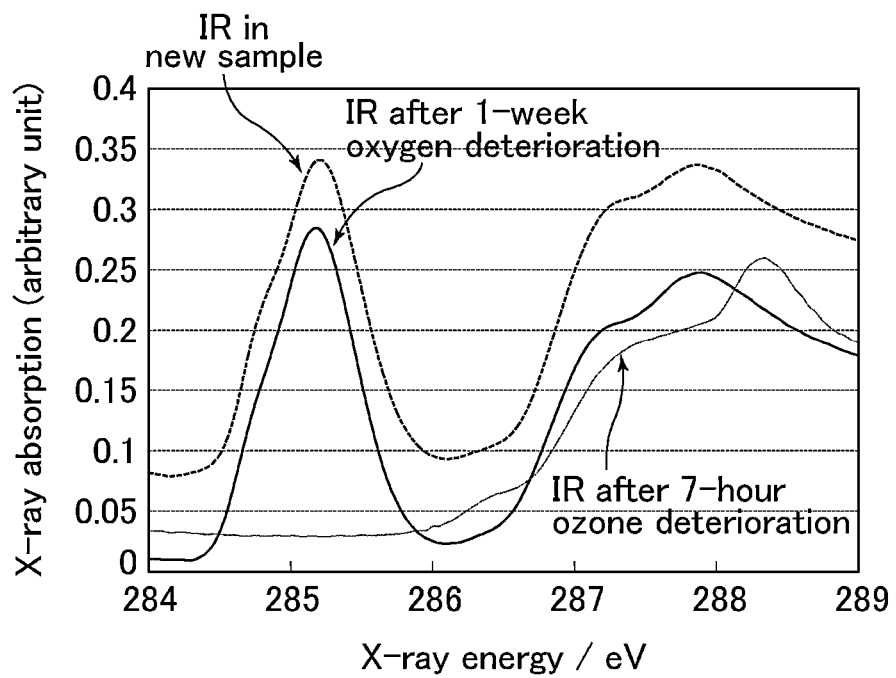
Figures 2, 3, 4:
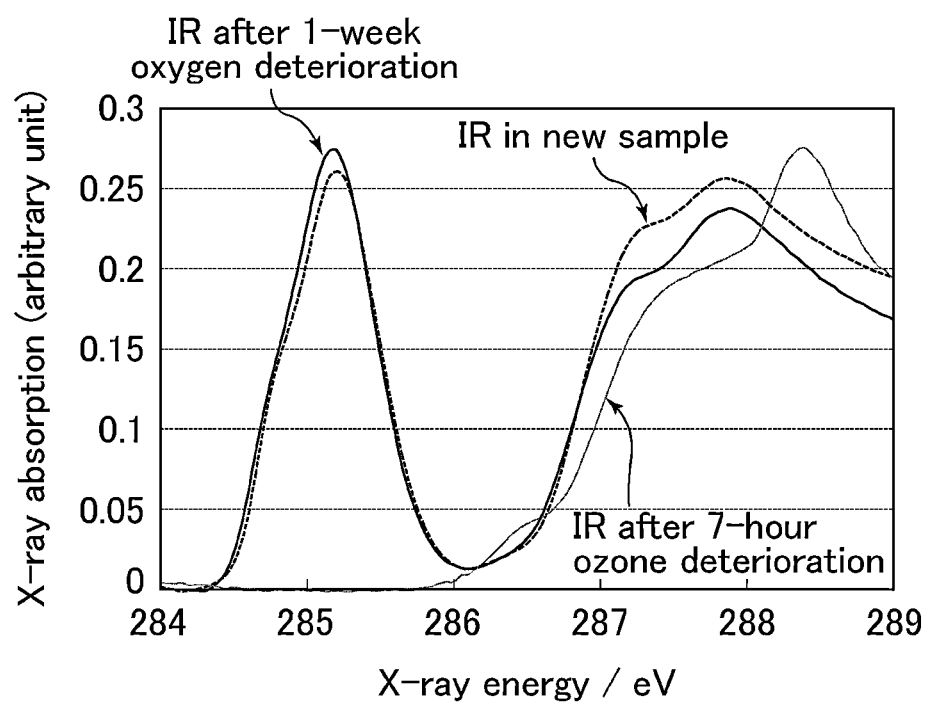
Figures 2, 3, 4, 5:
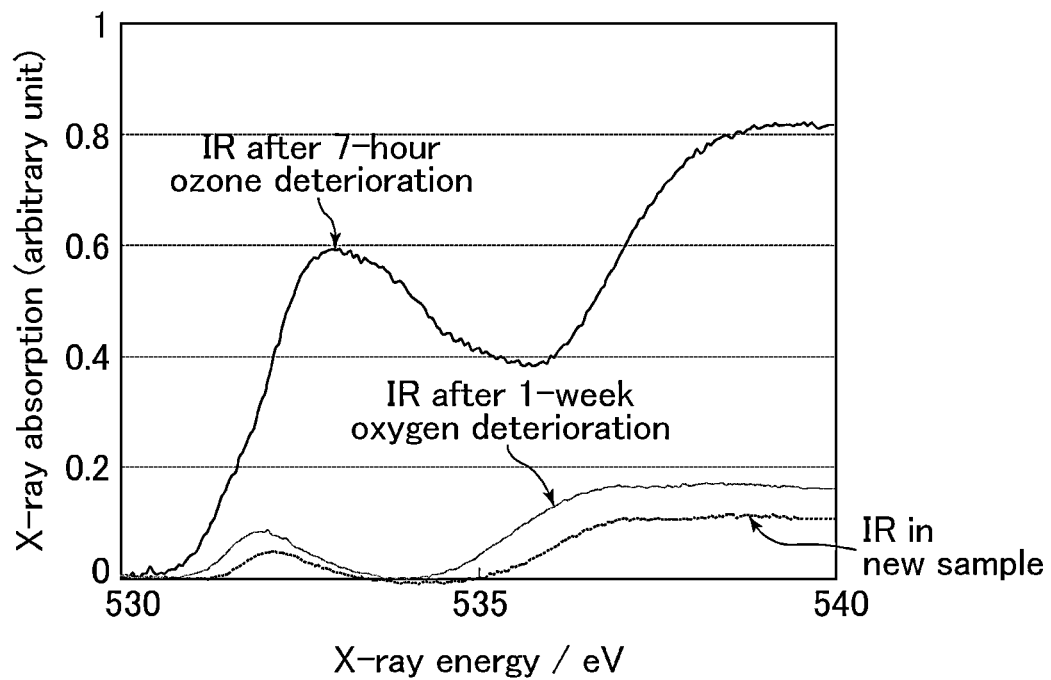
Figures 2, 3, 4, 5, 6:
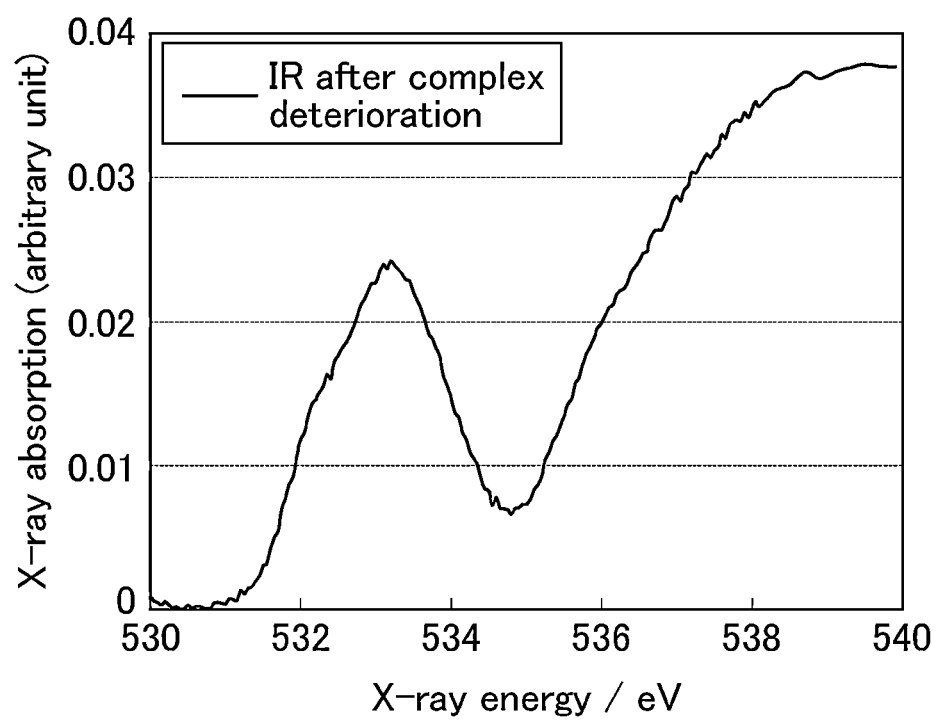
Figures 2, 3, 4, 5, 6, 7:
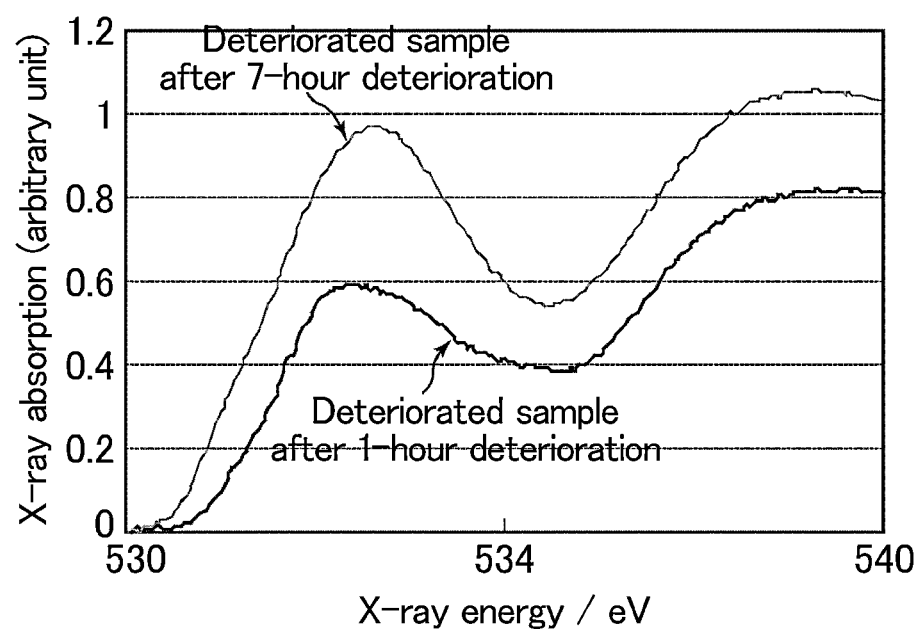
Figures 1, 3:
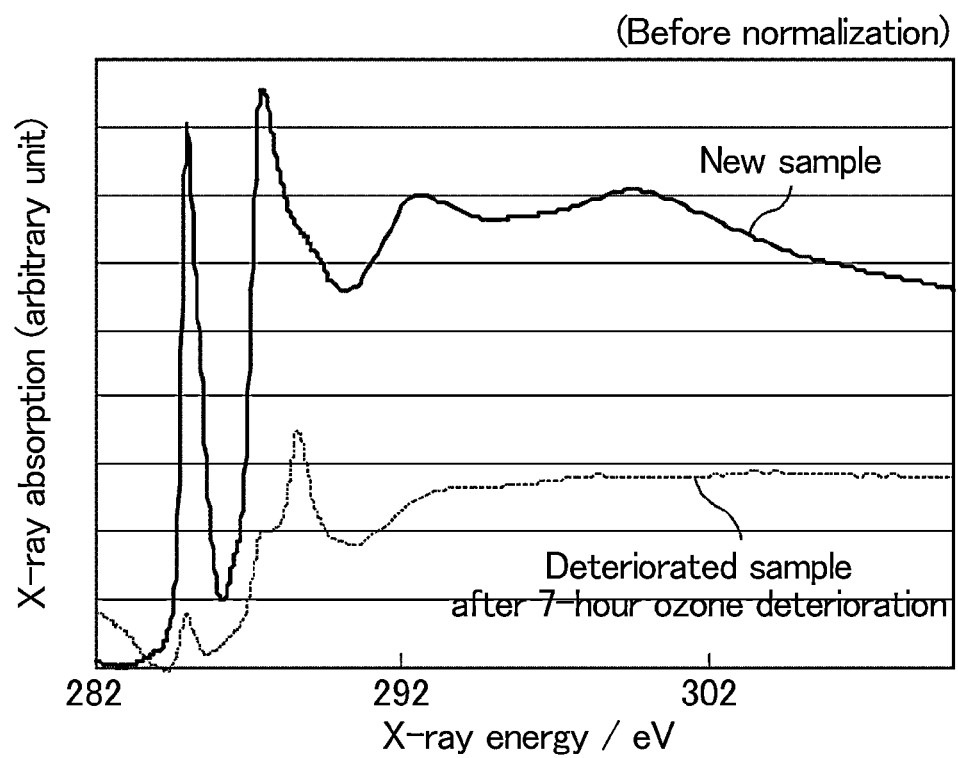
Figures 2, 3:
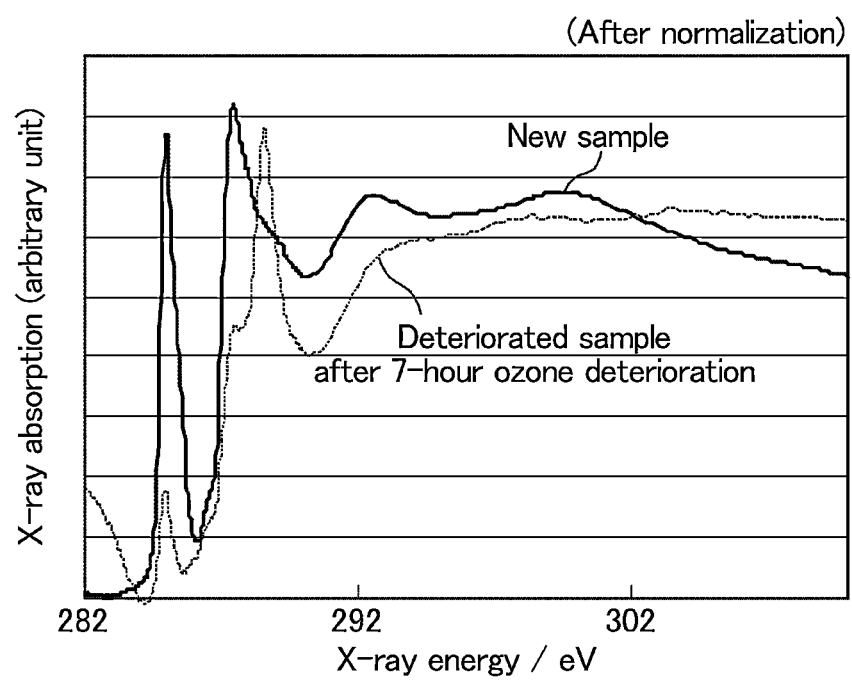
Figure 3:
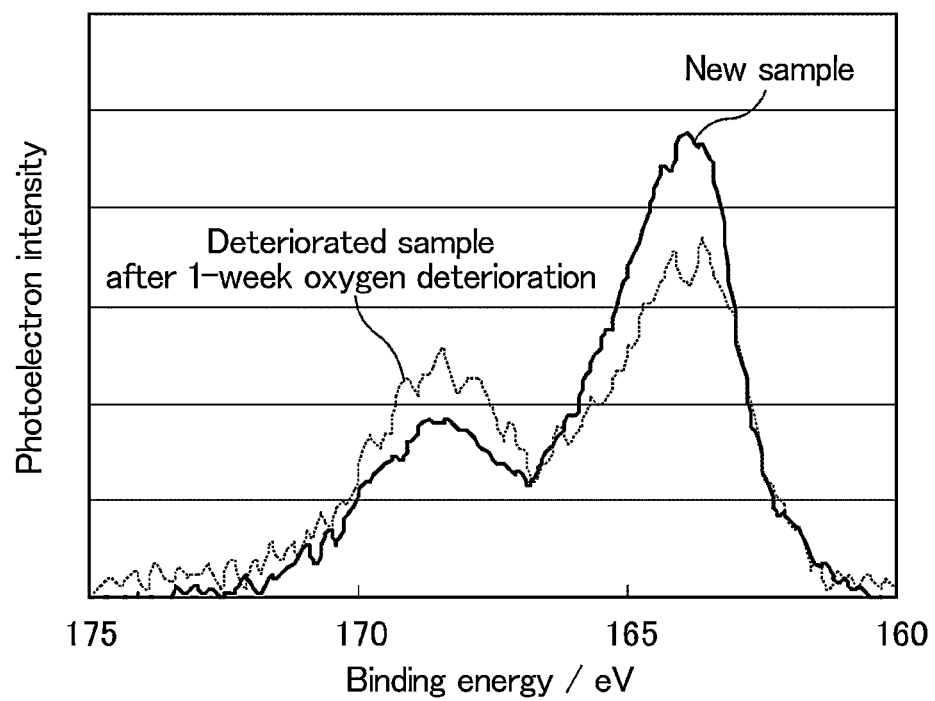
Figures 3, 4:
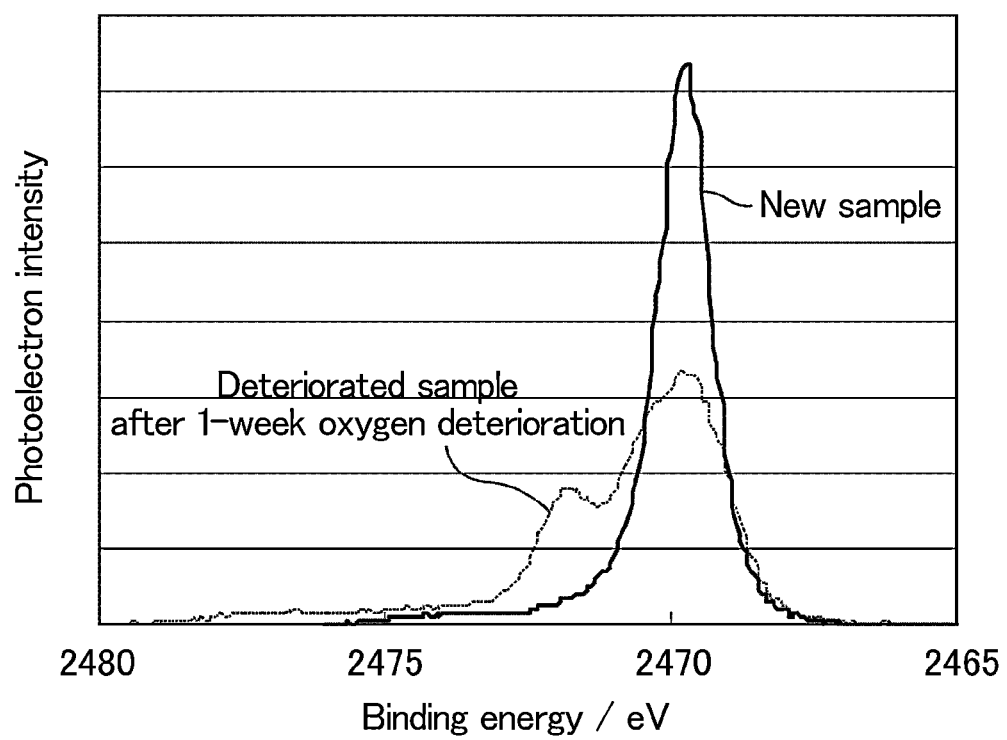

FIG. 2-4 shows the thus formed spectra of the carbon K-shell absorption edge after normalization. The degree of deterioration is determined using the Equation 2-2 based on the normalized spectra. The degree of deterioration herein refers to the rate of reduction of a $\pi^*$peak attributed to each diene polymer from before to after deterioration, and means the deterioration rate (%) of each diene polymer contained in a sample.

By performing the method of determining the degree of deterioration also on SBR, the degrees of deterioration of IR and SBR contained in a rubber blend can be individually analyzed.

In the method of determining the degree of deterioration, the degree of deterioration can also be determined by using the peak intensities, instead of the peak areas, in the Equation 2-2. The degree of deterioration can also be determined by the STXM method instead of the XPEEM method.

The second method of deterioration analysis may include: performing waveform separation of x-ray absorption spectra of each diene polymer around the oxygen K-shell absorption edge obtained by scanning over a range of high intensity x-ray energies of 500 to 600 eV; and calculating contribution rates of oxygen deterioration and ozone deterioration of each diene polymer according to Equations 2-3, wherein the oxygen deterioration corresponds to a peak on the low energy side with a peak top energy in the range of at least 532 eV but lower than 532.7 eV, and the ozone deterioration corresponds to a peak on the high energy side with a peak top energy in the range of at least 532.7 eV but not higher than 534 eV:

[Peak area of oxygen deterioration of diene polymer $Ai$]/[(Peak area of ozone deterioration of diene polymer $Ai$)+(Peak area of oxygen deterioration of diene polymer $Ai$)]×100=Contribution rate (%) of oxygen deterioration of diene polymer $Ai$, and

[Peak area of ozone deterioration of diene polymer $Ai$]/[(Peak area of ozone deterioration of diene polymer $Ai$)+(Peak area of oxygen deterioration of diene polymer $Ai$)]×100=Contribution rate (%) of ozone deterioration of diene polymer $Ai$, (Equations 2-3)

wherein $Ai$ represents each diene polymer contained in the polymer material.

In this manner, the contribution rates (%) of oxygen deterioration and ozone deterioration of each diene polymer in a deteriorated polymer material can be determined to allow analysis of the contribution rate of each deterioration factor.

In the method of calculating the contribution rates, the background is assessed based on a slope before the absorption edge and subtracted, prior to the calculation of Equations 2-3.

The method of calculating the contribution rates is more specifically described with reference to exemplary measurements of a new sample, a deteriorated sample after 7-hour ozone deterioration, and a deteriorated sample after 1-week oxygen deterioration of an IR/SBR rubber blend.

First, FIG. 2-5 shows the results of XPEEM measurement of IR at the oxygen K-shell absorption edge in a new sample, a deteriorated sample after 7-hour ozone deterioration, and a deteriorated sample after 1-week oxygen deterioration of an IR/SBR rubber blend. As shown in the figure, the ozone-deteriorated sample has a peak in the range of at least 532.7 eV but not higher than 534 eV, the oxygen-deteriorated sample has a peak in the range of at least 532 eV but lower than 532.7 eV. Of the two peaks, the peak on the high energy side is found to be attributed to ozone deterioration and the other peak on the low energy side is found to be attributed to oxygen deterioration.

Further, FIG. 2-6 shows the results of XPEEM measurement of IR near the oxygen K-shell absorption edge in a deteriorated sample after complex deterioration (oxygen deterioration and ozone deterioration). As shown in FIG. 2-6, a peak having two shoulders is detected at 532 to 534 eV. This is considered to be due to overlapping of the peak on the low energy side (at least 532 eV but lower than 532.7 eV) attributed to oxygen deterioration and the peak on the high energy side (at least 532.7 but not higher than 534 eV) attributed to ozone deterioration. Hence, peak separation was performed and then the contribution rates of oxygen deterioration and ozone deterioration were determined using the Equations 2-3. In this manner, a sample subjected to both oxygen deterioration and ozone deterioration can be analyzed for the proportion of each of the two deterioration factors, oxygen deterioration and ozone deterioration.

By performing the method of calculating the contribution rates also on SBR, the contribution rates of oxygen deterioration and ozone deterioration can be analyzed for each of IR and SBR contained in a rubber blend.

In the method of calculating the contribution rates, the contribution rates of oxygen deterioration and ozone deterioration can also be determined by using the peak intensities, instead of the peak areas, in the Equations 2-3. The contribution rates of oxygen deterioration and ozone deterioration can also be determined by the STXM method instead of the XPEEM method.

Another embodiment of the second method of deterioration analysis includes: determining a normalization constant $\gamma$ using Equation 2-4 based on an x-ray absorption spectrum of each diene polymer after deterioration around the carbon K-shell absorption edge; and correcting a total area of an x-ray absorption spectrum of each diene polymer around the oxygen K-shell absorption edge using Equation 2-5 with the normalization constant $\gamma$ to determine the amount of oxygen and ozone bonded to each diene polymer:

[Total area of x-ray absorption spectrum of diene polymer $Ai$ around carbon K-shell absorption edge]×$\gamma_{Ai}$=1, (Equation 2-4)

wherein $Ai$ represents each diene polymer contained in the polymer material; and

[Total area of x-ray absorption spectrum of diene polymer $Ai$ around oxygen K-shell absorption edge]$\times \gamma_{Ai}$=Amount (index) of oxygen and ozone bonded to diene polymer $Ai$, (Equation 2-5)

wherein $Ai$ represents each diene polymer contained in the polymer material.

In this manner, the amount of oxygen and ozone bonded to each diene polymer due to deterioration can be measured and used as a deterioration indicator.

In the method of determining the bonded amount, each of the total areas of the spectra is the integral of the spectrum over the measurement range. The energy range can be changed according to the measurement conditions and the like.

The method of determining the bonded amount is more specifically described with reference to exemplary measurements of a deteriorated sample after 7-hour ozone deterioration and a deteriorated sample after 1-hour ozone deterioration of an IR/SBR rubber blend.

FIG. 2-7 shows the measurement results of IR by the XPEEM method. In this measurement, a normalization constant γ is determined using the Equation 2-4 based on an x-ray absorption spectrum at the carbon K-shell absorption edge, and then normalization is performed using the Equation 2-5 as mentioned above. The normalized area of the oxygen K-shell absorption edge peak is considered to correspond to the amount of bonded oxygen and ozone. Since the sample subjected to 7-hour deterioration has a larger area than the sample subjected to 1-hour deterioration as shown in FIG. 2-7, the area values can be used as deterioration indices. A higher deterioration index refers to a larger amount of oxygen and ozone bonded to IR. Thus, the rate of deterioration by bonding of oxygen or ozone to IR can be determined based on the rate of increase in the area of the oxygen K-shell absorption edge peak.

By performing the method of calculating the deterioration rate also on SBR, the amount of oxygen and ozone bonded to each of IR and SBR contained in a rubber blend can be analyzed.

The amount of bonded oxygen and ozone can also be analyzed by the STXM method instead of the XPEEM method.

For example, the method of the second aspect of the present invention can be performed using a spectroscopic photoemission and low energy electron microscope (SPELEEM: product of Elimitec) attached to beamline BL17SU of SPring-8 in the case of the XPEEM method, and using beamline 5.3.2 of the Advanced Light Source (ALS) at the Lawrence Berkeley National Laboratory in the case of the STXM method.

The polymer material usable in the second aspect of the present invention is not particularly limited as long as it contains at least two diene polymers. Materials as mentioned for the first aspect of the present invention may be used. The method of deterioration analysis of the second aspect of the present invention can be suitably applied to these materials.

As mentioned above, new and deteriorated polymer materials containing multiple diene polymers are irradiated with high intensity x-rays while the energy of high intensity x-rays is varied, and then the degree of deterioration is assayed based on the x-ray absorption in a micro area of the polymer materials. This enables analysis of the deterioration of each diene polymer. Therefore, the method of the second aspect of the present invention can be used to analyze the degree of deterioration of each polymer component in commonly used blend materials and thus to develop materials that are less likely to deteriorate.

Next, the method of deterioration analysis of the third aspect of the present invention includes: irradiating a sulfur cross-linked polymer material with x-rays, and measuring x-ray absorption while varying the energy of the x-rays, to determine the deterioration of polymers; irradiating the sulfur cross-linked polymer material with constant energy x-rays, and measuring excited and emitted photoelectrons to determine the deterioration of sulfur crosslinks; and determining the deterioration ratio between polymers and sulfur crosslinks from the deterioration of polymers and the deterioration of sulfur crosslinks.

Known deterioration factors of sulfur cross-linked polymer materials such as rubber vulcanizates include deterioration of polymer molecular chains or sulfur crosslinks by ultraviolet light, oxygen, ozone, heat, and the like. In order to improve resistance to deterioration, it is important to know what factor is responsible and how the polymer molecular chains or cross-linked structures then change.

In this respect, the method of deterioration analysis of the third aspect of the present invention firstly focuses on the use of x-rays. In the method, new and deteriorated polymer materials are individually irradiated with x-rays while the energy of x-rays is varied, to measure the x-ray absorption, and then the resulting spectra are compared to analyze the deterioration of the deteriorated polymer material. Specifically, samples may be measured by a method of measuring an x-ray absorption spectrum near the absorption edge of a specific element (NEXAFS: Near Edge X-ray Absorption Fine Structure) or the like, and the deterioration of the polymer moiety can then be analyzed based on the peak area of the x-ray absorption spectrum at the carbon K-shell absorption edge, and the like.

When the NEXAFS method is used, the amount of oxygen, ozone and the like bonded to a polymer material can also be analyzed based on an x-ray absorption spectrum near the oxygen K-shell absorption edge. This method, however, cannot determine which moiety, the polymer moiety or sulfur-crosslink moiety, is bonded to oxygen or ozone. In the third aspect of the present invention, the deterioration of the polymer moiety (polymer molecular chains) is analyzed using x-rays, and the deterioration of sulfur crosslinks is also analyzed by the measurement of photoelectrons excited and emitted by irradiation with constant energy x-rays. Specifically, a sample may be measured by X-ray photoelectron spectroscopy (XPS) or the like, and the deterioration of sulfur crosslinks can then be analyzed based on the peak area attributed to sulfur and the like. Accordingly, the method of the third aspect of the present invention can be used to determine the degree of deterioration of each of polymers and sulfur crosslinks and thus to determine which is more deteriorated, polymers or sulfur crosslinks, i.e., to analyze the deterioration ratio between them.

In the case where the NEXAFS method is used to measure x-ray absorption while varying the energy of x-rays irradiated in the third aspect of the present invention, since the soft x-ray region includes the absorption edges of light elements, the chemical state of soft materials can be analyzed in detail.

The NEXAFS method can be carried out in the same manner as in the first method of deterioration analysis. In the third method of deterioration analysis, the brilliance of the x-rays, the number of photons of the x-rays, and the energy range scanned with the x-rays are preferably as mentioned for the brilliance of the high intensity x-rays, the number of photons of the high intensity x-rays, and the energy range scanned with the high intensity x-rays in the first method of deterioration analysis.

The NEXAFS method observes excitation to an unoccupied orbital, and thus allows great reflection of the impact of elements bonded to a target element. Accordingly, the present inventors have considered that the NEXAFS method can distinguish individual bonding states and thus can distinguish deterioration factors. This is why the NEXAFS method is used for the analysis of polymer deterioration in the third aspect of the present invention.

Specifically, the method can be carried out in the same manner as in the first method of deterioration analysis.

The electron yield method mentioned above may be used to measure and analyze x-ray absorption spectra of a polymer material and thereby assay the degree (%) of deterioration of polymers. This will be explained below.

In the third aspect of the present invention, for example, the method of determining the deterioration of polymers in a sulfur cross-linked polymer material by the NEXAFS method may include: calculating normalization constants $\alpha$ and $\beta$ using Equations 3-1 based on x-ray absorption spectra obtained by scanning over a required range of x-ray energies around the carbon K-shell absorption edge within the range of 260 to 400 eV; performing waveform separation of the x-ray absorption spectra around the carbon K-shell absorption edge corrected with the normalization constants $\alpha$ and $\beta$ to obtain peak areas attributed to $\pi$*transition at around 285 eV; and determining the degree (%) of deterioration of polymers using Equation 3-2 with the obtained peak areas:

[Total area of x-ray absorption spectrum over measurement range of sample before deterioration]× $\alpha$=1, and

[Total area of x-ray absorption spectrum over measurement range of sample after deterioration]× $\beta$=1; and  (Equations 3-1)

[1−[($\pi$*peak area after deterioration)×$\beta$]/[($\pi$*peak area before deterioration)×$\alpha$]]×100=Degree (%) of deterioration of polymers.  (Equation 3-2)

In this manner, the degree (%) of deterioration of polymers (polymer moiety) after deterioration can be determined to allow analysis of the deterioration rate. In the method of determining the degree of deterioration of polymers, the range of the x-ray energies is preferably from 260 to 350 eV. In the method of determining the degree of deterioration, the background is assessed based on a slope before the absorption edge and subtracted, prior to the calculation of Equations 3-1.

In the method of determining the degree of deterioration of polymers, each of the total areas of the x-ray absorption spectra in the Equations 3-1 is the integral of the spectrum over the measurement range. The energy range can be changed according to the measurement conditions and the like.

The method of determining the degree of deterioration of polymers is more specifically described referring to an example in which a new sample and a deteriorated sample after 7-hour ozone deterioration of a NR/BR rubber blend (both sulfur cross-linked) are used.

FIG. 3-1 shows the results of NEXAFS measurement of the carbon K-shell absorption edge in the samples. As shown in FIG. 3-1, the deteriorated sample has a smaller $\pi$* peak at around 285 eV than the new sample; however, an absolute measurement is difficult to perform by the NEXAFS method because subtle changes in the distance from the light source to the sample and the like affect the magnitude of the X-ray absorption spectrum. For this reason, the results of NEXAFS measurement of the carbon K-shell absorption edge cannot be simply compared between samples.

For comparison between the x-ray absorption spectra of the measured samples, the following normalization is performed (the x-ray absorption spectra of the samples are corrected for direct comparison). Since the amount of X-ray absorption of the shells of carbon does not change before and after deterioration, the peak area of the carbon K-shell absorption edge is normalized to 1 using the Equations 3-1. Specifically, normalization constants $\alpha$ and $\beta$ are first calculated using the Equations 3-1 based on the x-ray absorption spectra before normalization, and then the x-ray absorption spectra before normalization are corrected (normalized) by multiplying the spectra before normalization by $\alpha$ and $\beta$, whereby the $\pi$*peaks of the samples can be directly compared.

FIG. 3-2 shows the thus formed spectra at the carbon K-shell absorption edge after normalization. Based on the normalized spectra, the degree of deterioration of polymers is determined using the Equation 3-2. The degree of deterioration of polymers herein refers to the rate of reduction of $\pi$*peaks from before to after deterioration, and means the deterioration rate (%) of polymer chains in a sample.

In the method of determining the degree of deterioration of polymers, the degree of deterioration of polymers can also be determined by using the peak intensities, instead of the peak areas, in the Equation 3-2.

Although the description has been given on the case of an ozone-deteriorated sample, oxygen-deteriorated samples and samples deteriorated by both ozone and oxygen can also be similarly analyzed to determine the degree of deterioration of polymer chains.

The analysis of the deterioration of polymers in the third aspect of the present invention can be carried out using, for example, beamline BL12 at Kyushu Synchrotron Light Research Center in Saga, Japan.

Further, in the third aspect of the present invention, the sulfur cross-linked polymer material is irradiated with constant energy x-rays, and then excited and emitted photoelectrons are measured to determine the deterioration of sulfur crosslinks. The determination of the deterioration of sulfur crosslinks in addition to the deterioration of polymers allows analysis of the deterioration ratio between them.

The method of irradiating a sulfur cross-linked polymer material with constant energy x-rays and measuring excited and emitted photoelectrons may be X-ray photoelectron spectroscopy (XPS). Specifically, measurement can be performed by the conventional XPS method with Al K$\alpha_1$ radiation (1486.6 eV), hard X-ray photoemission spectroscopy (HAX-PES), or the like.

In the third aspect of the present invention, an exemplary method (method 1) of determining the deterioration of sulfur crosslinks by the XPS method includes: dispersing the photoelectrons excited and emitted by irradiation with the constant energy x-rays; measuring S2p photoelectron intensity to obtain an x-ray photoelectron spectrum; performing waveform separation of the spectrum to obtain a peak area attributed to sulfur oxides; and determining degree (%) of deterioration of sulfur crosslinks using Equation 3-3 with the obtained peak area:

(S2p peak area attributed to sulfur oxides)/(Total S2p peak area)×100=Degree (%) of deterioration of sulfur crosslinks.  (Equation 3-3)

In this manner, the degree (%) of deterioration of the sulfur crosslink moiety after deterioration can be determined to allow analysis of the deterioration rate.

In the method 1, the total S2p peak area in the Equation 3-3 is the integral of the spectrum over the measurement range. The energy range can be changed according to the measurement conditions and the like.

In the method 1, the energy range of the constant energy x-rays used is preferably from 150 to 200 eV, and more preferably from 155 to 180 eV, because such x-rays allow the measurement of the S2p (sulfur 2p orbital) peak area.

The method 1 is more specifically described referring to an example in which a new sample and a deteriorated sample after 1-week deterioration by heat and oxygen of a NR/BR rubber blend (both sulfur cross-linked) are used.

FIG. 3-3 shows the measurement results of S2p (sulfur 2p orbital) x-ray photoelectron spectra of these polymer material samples. As shown in FIG. 3-3, in the deteriorated sample, a peak corresponding to the S—S bond is reduced while a peak corresponding to sulfur oxides ($SO_x$) is increased. Accordingly, the degree (%) of deterioration of sulfur crosslinks can be determined by performing waveform separation of the S2p x-ray photoelectron spectrum of a deteriorated sample to obtain peaks corresponding to the S—S bond and $SO_x$, and then applying the peak area attributed to $SO_x$ and the total S2p peak area to the Equation 3-3.

It is considered that two peaks appears for each attribution in the S2p orbital due to spin-orbit splitting and that the sulfur oxide ($SO_x$) peak is formed of multiple peaks differing in valence overlapped. In principle, as shown in FIG. 3-3, the peak attributed to S—S and the peak attributed to $SO_x$ can be roughly divided.

In the method 1, the degree (%) of deterioration of sulfur crosslinks can also be determined by using the peak intensities, instead of the peak areas, in the Equation 3-3.

Moreover, an exemplary method (method 2) of determining the deterioration of sulfur crosslinks by the HAX-PES method includes: dispersing the photoelectrons excited and emitted by irradiation with the constant energy x-rays; measuring S1s photoelectron intensity to obtain an x-ray photoelectron spectrum; performing waveform separation of the spectrum to obtain a peak area attributed to sulfur oxides; and determining the degree (%) of deterioration of sulfur crosslinks using Equation (3-4) with the obtained peak area:

($S1s$ peak area attributed to sulfur oxides)/(Total $S1s$ peak area)×100=Degree (%) of deterioration of sulfur crosslinks. (Equation 3-4)

In this manner, the degree (%) of deterioration of sulfur crosslinks after deterioration can be determined to allow analysis of the deterioration rate.

In particular, the HAX-PES method advantageously allows measurement of the S1s orbital which cannot be measured by the conventional XPS method. Specifically, the conventional XPS method, which measures S2p orbital spectra, has a detection depth ranging from the surface to several nanometers as it uses low energy x-rays. In contrast, the HAX-PES method allows measurement of the S1s orbital and has a detection depth ranging from the surface to several tens of nanometers as it uses high energy x-rays. Accordingly, in the XPS method which measures the very top surface, the measurement results may be affected by blooms of a sulfur compound formed on the very top surface of a sulfur cross-linked polymer material such as a rubber sample. In the HAX-PES method with deep detection depth, on the other hand, the measurement results are presumably not affected by such blooms. Thus, the HAX-PES method enables especially bulk (inside) analysis of the deterioration of sulfur crosslinks in a sulfur cross-linked polymer material.

Also in cases where S2p orbital spectra are measured by the conventional XPS method, the effect of blooms on the measurement results can be reduced by removing the very top surface of a sample by argon ion etching or the like before the measurement.

In the method 2, the total S1s peak area in the Equation 3-4 is the integral of the spectrum over the measurement range. The energy range can be changed according to the measurement conditions and the like.

In the method 1, the energy range of constant energy x-rays used is preferably from 2.5 to 15 keV, and more preferably from 4 to 10 keV, because such x-rays allow the measurement of the S1s (sulfur 1s orbital) peak area.

The method 2 is more specifically described referring to an example in which a new sample and a deteriorated sample after 1-week deterioration by heat and oxygen of a NR/BR rubber blend (both sulfur cross-linked) are used.

FIG. 3-4 shows the measurement results of S1s (sulfur is orbital) x-ray photoelectron spectra of these polymer material samples. As shown in FIG. 3-4, in the deteriorated sample, a peak corresponding to the S—S bond is reduced while a peak corresponding to sulfur oxides ($SO_x$) is increased. Accordingly, the degree (%) of deterioration of sulfur crosslinks can be determined by performing waveform separation of the S1s x-ray photoelectron spectrum of a deteriorated sample to obtain peaks corresponding to the S—S bond and $SO_x$, and then applying the peak area attributed to $SO_x$ and the total sulfur peak area to the Equation 3-4.

It is considered that the sulfur oxide ($SO_x$) peak is formed of multiple peaks differing in valence overlapped. In principle, as shown in FIG. 3-4, the peak attributed to S—S and the peak attributed to $SO_x$ can be roughly divided.

In the method 2, the degree (%) of deterioration of sulfur crosslinks can also be determined by using the peak intensities, instead of the peak areas, in the Equation 3-4.

Although the descriptions in the methods 1 and 2 have been given on the cases of oxygen-deteriorated samples, ozone-deteriorated samples and samples deteriorated by both ozone and oxygen can also be similarly analyzed to determine the degree of deterioration of sulfur crosslinks.

The analysis of the deterioration of sulfur crosslinks in the third aspect of the present invention can be carried out using, for example, a common XPS device such as AXIS Ultra produced by Kratos or a HAX-PES device attached to beamline BL46XU of SPring-8.

Further, in the method of deterioration analysis according to the third aspect of the present invention, for example, the contribution ratio of deterioration of polymers and deterioration of sulfur crosslinks can be calculated from Equation 3-5:

[Degree (%) of deterioration of polymers]/[Degree (%) of deterioration of sulfur crosslinks]=Contribution ratio of deterioration of polymers and deterioration of sulfur crosslinks.

Specifically, the method of determining the degree of deterioration of polymers and the method of determining the degree of deterioration of sulfur crosslinks, for example, can be used to determine the ratio (proportion) of the degree (%) of deterioration of polymers and the degree (%) of deterioration of sulfur crosslinks, which indicate the degrees of deterioration of polymers and of sulfur crosslinks, respectively. This makes it possible to determine which is more deteriorated, polymers or sulfur crosslinks. More specifically, in the Equation 3-5, polymers are considered to be more deteriorated in the case of (contribution ratio of deterioration of polymers to deterioration of sulfur crosslinks)>1, and sulfur crosslinks are considered to more deteriorated in the case of (contribution ratio of deterioration of polymers to deterioration of sulfur crosslinks)<1. Thus, the method of the third aspect of the present invention can be used to take more effective measures against deterioration than conventional measures.

The sulfur cross-linked polymer material usable in the third aspect of the present invention is not particularly limited, and may be a conventionally known one. It may suitably be a sulfur cross-linked rubber material containing at least one diene rubber, or a composite material formed by combining the rubber material and at least one resin followed by sulfur cross-linking. The diene rubber and the resin may be materials as mentioned in the first aspect of the present invention. The method of deterioration analysis according to the third aspect of the present invention can be suitably applied to these materials.

EXAMPLES

The present invention is more specifically described with reference to, but not limited to, examples.

Examples 1-1 to 1-5, Comparative Example 1-1

Deteriorated samples used in the examples and comparative example were prepared from the following rubber materials under the following deterioration conditions. For measurement by the NEXAFS method, samples were processed to have a thickness of at most 100 μm using a microtome. Then the prepared samples were stored in a vacuum desiccator to avoid the effects of oxygen other than deterioration.

(Rubber Material)
 IR: Nipol IR 2200 from ZEON CORPORATION
 BR: Ubepol BR 130B from UBE INDUSTRIES, LTD.
 SBR: Nipol 1502 from ZEON CORPORATION
 NR: TSR20 from Hainan Sinochem Rubber Co., Ltd.
 Product after driving in North America: Tire (made of NR/BR rubber blend) having been driven in North America Product after driving in Middle East: Tire (made of NR/BR rubber blend) having been driven in Middle East
(Deterioration Conditions)
 Ozone deterioration: 40° C., 50 pphm (1 hour)
 Oxygen deterioration: 80° C. in the air (7 days)
(Device)
 NEXAFS: NEXAFS device attached to beamline BL12 at Kyushu Synchrotron Light Research Center in Saga, Japan
 XPS: AXIS Ultra from Kratos The degree (%) of deterioration of each sample was measured by performing the following analysis of the deterioration rate by NEXAFS.

The following NEXAFS measurement conditions were used.
 Brilliance: $5 \times 10^{12}$ photons/s/mrad$^2$/mm$^2$/0.1% bw
 Number of photons: $2 \times 10^9$ photons/s
(Analysis of Degree of Deterioration)

Scanning was performed over a range of high intensity x-ray energies of 260 to 400 eV to obtain x-ray absorption spectra around the carbon K-shell absorption edge. Normalization constants α and β were calculated from Equations 1-1 based on the spectra over the required range from 260 to 350 eV, and then the spectra were normalized (corrected) with the obtained constants. The peaks attributed to π*transition at around 285 eV in the normalized spectra were subjected to waveform separation using a Gaussian function to obtain peaks attributed to each polymer component. The degree (%) of deterioration of each polymer component was determined using Equation 1-2 with the peak areas attributed to it.

In Comparative Example 1-1, the deteriorated sample was evaluated by XPS.

Table 1 shows the results of the above analysis.

TABLE 1

|  |  | Comparative Example 1-1 | Example 1-1 | Example 1-2 | Example 1-3 | Example 1-4 NEXAFS | Example 1-5 NEXAFS |
|---|---|---|---|---|---|---|---|
| Measurement method |  | XPS | NEXAFS | NEXAFS | NEXAFS | Rubber blend 3 (after driving in North America) | Rubber blend 4 (after driving in Middle East) |
| Rubber blend |  | Rubber blend 1 | Rubber blend 1 | Rubber blend 2 | Rubber blend 1 |  |  |
| Component | Polymer 1 | IR | IR | SBR | IR | NR | NR |
|  | Polymer 2 | BR | BR | BR | BR | BR | BR |
| Deterioration conditions |  | Ozone deterioration | Ozone deterioration | Ozone deterioration | Oxygen deterioration | — | — |
| Degree (%) of deterioration of Polymer 1 |  | Not calculable | 41 | 11 | 0 | 57 | 7 |
| Degree (%) of deterioration of Polymer 2 |  | Not calculable | 21 | 19 | 12 | 42 | 29 |

In Comparative Example 1-1 using XPS, the degree of deterioration of each diene polymer contained in the rubber blend was not individually analyzable. In contrast, in Examples 1-1 to 1-5 using NEXAFS, the degree of deterioration was analyzable for each polymer component by performing waveform separation of the π*transition peaks to obtain peaks from each diene polymer. This proved the effectiveness of the evaluation method according to the first aspect of the present invention. Accordingly, the method according to the first aspect of the present invention can be expected to be employed for measures against deterioration of polymer materials containing at least two diene polymers, such as tires, and the like.

Examples 2-1 and 2-2, Comparative Examples 2-1 and 2-2

Deteriorated samples used in the examples and comparative examples were prepared from the following rubber materials under the following deterioration conditions. For measurement by the XPEEM and TEM methods, samples were processed to have a thickness of at most 100 μm using a microtome. Then the prepared samples were stored in a vacuum desiccator to avoid the effects of oxygen other than deterioration.

(Rubber Material)
IR: Nipol IR 2200 from ZEON CORPORATION
NR: TSR20 from Hainan Sinochem Rubber Co., Ltd.
SBR: SBR1502 from LG Chemical
Product after driving in North America: Tire (made of NR/SBR rubber blend) having been driven in North America
(Deterioration Conditions)
Ozone deterioration: 40° C., 50 pphm (1 hour)
(Device)
XPEEM: Spectroscopic photoemission and low energy electron microscope (SPELEEM: product of Elmitec) attached to beamline BL17SU of SPring-8
TEM: JEM2100F from JEOL Ltd.

The degree (%) of deterioration of each sample was measured by performing the following analysis of the deterioration rate by XPEEM.

(Analysis of Deterioration Contribution Rate)

Scanning was performed over a range of high intensity x-ray energies of 500 to 600 eV to obtain an x-ray absorption spectrum of each polymer component around the oxygen K-shell absorption edge. The spectrum was subjected to waveform separation, and then the contribution rates of oxygen deterioration and ozone deterioration of each polymer component were calculated from Equations 2-3, wherein the oxygen deterioration corresponds to a peak on the low energy side with a peak top of at least 532 eV but lower than 532.7 eV, and the ozone deterioration corresponds to a peak on the high energy side with a peak top of at least 532.7 eV but not higher than 534 eV.

(Determination of Deterioration Indicator)

A normalization constant γ for each polymer component was determined using Equation 2-4 based on the x-ray absorption spectrum around the carbon K-shell absorption edge after deterioration obtained in the analysis of the deterioration rate. The total area of the oxygen K-shell absorption edge was corrected (normalized) using Equation 2-5 with the obtained constant to determine the amount of oxygen and ozone bonded to each polymer component (deterioration indicator).

In Comparative Examples 2-1 and 2-2, the deteriorated samples were evaluated by TEM.

Table 2 shows the results of the above analysis.

TABLE 2

|  |  | Comparative Example 2-1 | Example 2-1 | Comparative Example 2-2 | Example 2-2 |
|---|---|---|---|---|---|
| Measurement method |  | TEM (Osmium staining) | XPEEM | TEM (Osmium staining) | XPEEM |
| Rubber blend |  | Rubber blend 1 | Rubber blend 1 | Rubber blend 2 (After driving in North America) | Rubber blend 2 (After driving in North America) |
| Component | Polymer 1 | IR | IR | NR | NR |
|  | Polymer 2 | SBR | SBR | SBR | SBR |
| Observation of each polymer |  | ○ | ○ | ○ | ○ |
| Polymer 1 | Degree (%) of deterioration | Not calcurable | 49 | Not calcurable | 67 |
|  | Contribution rate (%) of oxygen deterioration | Not calcurable | 0 | Not calcurable | 50 |
|  | Contribution rate (%) of ozone deterioration | Not calcurable | 100 | Not calcurable | 61 |
|  | Amount (index) of bonded oxygen and ozone | Not calcurable | 0.53 | Not calcurable | 0.7 |
| Polymer 2 | Degree (%) of deterioration | Not calcurable | 28 | Not calcurable | 52 |
|  | Contribution rate (%) of oxygen deterioration | Not calcurable | 0 | Not calcurable | 40 |
|  | Contribution rate (%) of ozone deterioration | Not calcurable | 100 | Not calcurable | 49 |
|  | Amount (index) of bonded oxygen and ozone | Not calcurable | 0.33 | Not calcurable | 0.56 |

The following XPEEM measurement conditions were used.
Number of photons: $1 \times 10^{11}$ photons/s
(Observation of Each Polymer)
In the case where external observation was possible for each polymer blended in each sample, "0" is displayed.
(Analysis of Degree of Deterioration)

Scanning was performed over a range of high intensity x-ray energies of 260 to 400 eV to obtain x-ray absorption spectra of each polymer component around the carbon K-shell absorption edge. Normalization constants α and β for each polymer component were calculated from Equations 2-1 based on the spectra over the required range from 260 to 350 eV, and then the spectra were normalized (corrected) with the obtained constants. The normalized spectra were subjected to waveform separation, and then the degree (%) of deterioration of each polymer component was determined using Equation 2-2 with the resulting peak areas attributed to π*transition at around 285 eV.

In Comparative Example 2-1 and 2-2 using TEM, the degree of deterioration, the contribution rate of oxygen deterioration, the contribution rate of ozone deterioration, and the amount of bonded oxygen and ozone of each diene polymer contained in the rubber blend were not individually analyzable. In contrast, in Examples 2-1 and 2-2 using XPEEM, these items were individually analyzable by measuring the x-ray absorption spectra for each diene polymer contained in the rubber blend. This proved the effectiveness of the evaluation method according to the second aspect of the present invention.

Accordingly, the method of the second aspect of the present invention can be expected to be employed for measures against deterioration of polymer materials containing at least two diene polymers, such as tires, and the like.

Examples 3-1 to 3-8, Comparative Examples 3-1 to 3-4

Deteriorated samples used in the examples and comparative examples were prepared from the following rubber materials under the following deterioration conditions. For measurement by the NEXAFS method, samples were processed to have a thickness of at most 100 µm using a microtome. Then the prepared samples were stored in a vacuum desiccator to avoid the effects of oxygen other than deterioration.
(Rubber Material)
NR/BR rubber blend (sulfur cross-linked): TSR20 from Hainan Sinochem Rubber Co., Ltd., Ubepol BR 130B from UBE INDUSTRIES, LTD.
Product after driving in Middle East: Tire (made of NR/BR rubber blend (sulfur cross-linked); sidewall was used) having been driven in Middle East
(Deterioration Conditions)
Ozone deterioration: 40° C., 50 pphm
Oxygen deterioration: 80° C. in the air
(Device)
NEXAFS: NEXAFS device attached to beamline BL12 at Kyushu Synchrotron Light Research Center in Saga, Japan
XPS: AXIS Ultra from Kratos
HAX-PES: HAX-PES device attached to beamline BL46XU of SPring-8

The degree (%) of deterioration of polymers was determined by performing the following analysis on each sample before and after deterioration by NEXAFS.
The following NEXAFS measurement conditions were used.
Brilliance: $5 \times 10^{12}$ photons/s/mrad$^2$/mm$^2$/0.1% bw
Number of photons: $2 \times 10^9$ photons/s
(Analysis of Degree of Deterioration of Polymers)
Scanning was performed over a range of high intensity x-ray energies of 260 to 400 eV to obtain x-ray absorption spectra around the carbon K-shell absorption edge. Normalization constants $\alpha$ and $\beta$ were calculated from Equations 3-1 based on the spectra over the required range from 260 to 350 eV, and then the spectra were normalized (corrected) with the obtained constants. The normalized spectra were subjected to waveform separation, and then the degree (%) of deterioration of polymers was determined using Equation 3-2 with the resulting peak areas attributed to π*transition at around 285 eV.

The degree (%) of deterioration of sulfur crosslinks of each deteriorated sample was determined by performing the following analysis according to the method 1 with XPS.
The following XPS measurement conditions were used.
Measurement light source: Al (monochromator)
Energy of irradiated x-rays: 1486 eV
Measurement output: 20 kV×10 mA
Measured element and orbital: S 2p
Binding energy: 163.6 eV (S2p1/2), 162.5 eV (S2p3/2)
(Analysis of Degree of Deterioration of Sulfur Crosslinks (Method 1))
Photoelectrons excited and emitted by irradiation with the constant energy x-rays were dispersed, and the S2p photoelectron intensity was measured to obtain an X-ray photoelectron spectrum. The spectrum over a range from 160 to 175 eV was subjected to waveform separation to obtain a peak corresponding to the S—S bond at around 164 eV and a peak corresponding to SO$_x$ at around 168 eV. Then the degree (%) of deterioration of sulfur crosslinks was determined using Equation 3-3 with the peak area attributed to sulfur oxides and the total sulfur peak area over a range from 160 to 175 eV.

The degree (%) of deterioration of sulfur crosslinks of each deteriorated sample was determined by performing the following analysis according to the method 2 with HAX-PES.
The following HAX-PES measurement conditions were used.
Measurement light source: High intensity x-rays
Energy of irradiated x-rays: 8 keV
Measurement output: $10^{13}$ photon/s
Measured element and orbital: S1s
Binding energy: 2472 eV
(Analysis of Degree of Deterioration of Sulfur Crosslinks (Method 2))
Photoelectrons excited and emitted by irradiation with the constant energy x-rays were dispersed, and the S1s photoelectron intensity was measured to obtain an X-ray photoelectron spectrum. The spectrum over a range from 2465 to 2480 eV was subjected to waveform separation to obtain a peak corresponding to the S—S bond at around 2470 eV and a peak corresponding to SO$_x$ at around 2472 eV. Then the degree (%) of deterioration of sulfur crosslinks was determined using Equation 3-4 with the peak area attributed to sulfur oxides and the total sulfur peak area over a range from 2465 to 2480 eV.
(Analysis of Contribution Ratio of Deterioration of Polymers and Deterioration of Sulfur Crosslinks)
The contribution ratio of deterioration of polymers and deterioration of sulfur crosslinks was calculated by applying, to Equation 3-5, the numerical values of the degree of deterioration of polymers and the degree of deterioration of sulfur crosslinks determined in the analysis of the degree of deterioration of polymers and the degree of deterioration of sulfur crosslinks (methods 1 and 2).
Table 3-1 shows the results of the analysis of the degree of deterioration of polymers and the degree of deterioration of sulfur crosslinks (method 1). Table 3-2 shows the results of the analysis of the degree of deterioration of polymers and the degree of deterioration of sulfur crosslinks (method 2).

TABLE 3-1

|  | Comparative Example 3-1 | Comparative Example 3-2 | Example 3-1 | Example 3-2 |
| --- | --- | --- | --- | --- |
| Measurement method | Swell | FTIR | NEXAFS | NEXAFS |
| Material | NR/BR | NR/BR | NR/BR | NR/BR |
| Deterioration time (h)/ozone | 24 h | 24 h | 96 h | 0 h |
| Deterioration time (h)/heat and oxygen | 0 h | 0 h | 0 h | 168 h |
| Degree (%) of deterioration of polymers | — | — | 42.0 | 21.7 |
| Degree (%) of deterioration of sulfur crosslinks | — | — | 29.1 | 42.0 |
| Contribution ratio (%) | — | — | 1.44 | 0.52 |

|  | Example 3-3 | Example 3-4 |
| --- | --- | --- |
| Measurement method | NEXAFS | NEXAFS |
| Material | Product after driving in Middle East | Product after driving in Middle East |

TABLE 3-1-continued

| | | |
|---|---|---|
| Degree (%) of deterioration of polymers | 26.9 | 17.8 |
| Degree (%) of deterioration of sulfur crosslinks | 80.8 | 47.5 |
| Contribution ratio (%) | 0.33 | 0.37 |

TABLE 3-2

| | Comparative Example 3-3 | Comparative Example 3-4 | Example 3-5 | Example 3-6 |
|---|---|---|---|---|
| Measurement method | Swell | FTIR | NEXAFS | NEXAFS |
| Material | NR/BR | NR/BR | NR/BR | NR/BR |
| Deterioration time (h)/ozone | 24 h | 24 h | 96 h | 0 h |
| Deterioration time (h)/heat and oxygen | 0 h | 0 h | 0 h | 168 h |
| Degree (%) of deterioration of polymers | — | — | 42.0 | 21.7 |
| Degree (%) of deterioration of sulfur crosslinks | — | — | 13.8 | 33.8 |
| Contribution ratio (%) | — | — | 3.01 | 0.64 |

| | Example 3-7 | Example 3-8 |
|---|---|---|
| Measurement method | NEXAFS | NEXAFS |
| Material | Product after driving in Middle East | Product after driving in Middle East |
| Degree (%) of deterioration of polymers | 26.9 | 17.8 |
| Degree (%) of deterioration of sulfur crosslinks | 41.4 | 10.8 |
| Contribution ratio (%) | 0.65 | 1.65 |

In Comparative Examples 3-1 to 3-4 using Swell or FT-IR, none of the degree of deterioration of polymers, the degree of deterioration of sulfur crosslinks, and the contribution ratio of the deteriorated samples was not analyzable. In contrast, in Examples 3-1 to 3-4 using NEXAFS and XPS, and in Examples 3-5 to 3-8 using NEXAFS and HAX-PES, all of these items were analyzable. This proved the effectiveness of the evaluation method according to the third aspect of the present invention. Especially in the case of using HAX-PES, since the effect of blooms on the sample surface is presumably avoided, the results of Examples 3-5 to 3-8 are considered to be more reliable.

The invention claimed is:

1. A method of oxygen and/or ozone deterioration analysis, comprising:
subjecting a polymer material containing at least two diene polymers to oxygen and/or ozone deterioration;
irradiating the polymer material containing at least two diene polymers with high intensity x-rays at multiple different wavelengths in sequence in the energy range of 260 to 400 eV; and
measuring x-ray absorption correspondingly for each energy irradiation in sequence while varying the energy of the x-rays, to analyze deterioration of each diene polymer;
wherein the method comprises:
calculating normalization constants $\alpha$ and $\beta$ using Equations 1-1 from x-ray absorption spectra obtained by scanning over a range of high intensity x-ray energies around the carbon K-shell absorption edge within the range of 260 to 400 eV;
performing waveform separation of the x-ray absorption spectra around the carbon K-shell absorption edge corrected with the normalization constants $\alpha$ and $\beta$ to obtain peaks attributed to $\pi^*$ transition at around 285 eV; and
determining degree of deterioration of each diene polymer using Equation 1-2 with areas of the obtained peaks:

[Total area of x-ray absorption spectrum over measurement range of sample before deterioration]× $\alpha$=1, and

[Total area of x-ray absorption spectrum over measurement range of sample after deterioration]× $\beta$=1; and    (Equations 1-1)

[1−[($\pi^*$peak area of each diene polymer after deterioration)×$\beta$]/[($\pi^*$peak area of each diene polymer before deterioration)×$\alpha$]]×100=Degree (%) of deterioration.    (Equation 1-2)

2. The method according to claim 1, wherein the high intensity x-rays have a brilliance of at least $10^{10}$ (photons/s/mrad$^2$/mm$^2$/0.1% bw).

3. The method according to claim 1, wherein peak intensities are used instead of the peak areas.

4. A method of oxygen and/or ozone deterioration analysis, comprising:
subjecting a polymer material containing at least two diene polymers to oxygen and/or ozone deterioration;
irradiating the polymer material containing at least two diene polymers with high intensity x-rays at multiple different wavelengths in sequence in the energy range of 260 to 400 eV; and
measuring x-ray absorption correspondingly for each energy irradiation in sequence in a micro area of the polymer material while varying the energy of the x-rays, to analyze deterioration of each diene polymer,
wherein the method comprises:
calculating normalization constants $\alpha$ and $\beta$ using Equations 2-1 from x-ray absorption spectra of each diene polymer obtained by scanning over a range of high intensity x-ray energies around the carbon K-shell absorption edge within the range of 260 to 400 eV;
performing waveform separation of the x-ray absorption spectra around the carbon K-shell absorption edge corrected with the normalization constants $\alpha$ and $\beta$ to obtain peak areas attributed to $\pi^*$ transition at around 285 eV; and
determining degree of deterioration of each diene polymer using Equation 2-2 with the obtained peak areas:

[Total area of x-ray absorption spectrum of diene polymer $Ai$ in sample before deterioration]× $\alpha_{Ai}$=1, and

[Total area of x-ray absorption spectrum of diene polymer $Ai$ in sample after deterioration]× $\beta_{Ai}$=1,    (Equations 2-1)

wherein Ai represents each diene polymer contained in the polymer material; and

[1−[($\pi^*$ peak area of diene polymer $Ai$ after deterioration)×$\beta_{Ai}$]/[($\pi^*$ peak area of diene polymer $Ai$ before deterioration)×$\alpha_{Ai}$]]×100=Degree (%) of deterioration of diene polymer $Ai$,    (Equation 2-2)

wherein Ai represents each diene polymer contained in the polymer material.

5. The method according to claim 4, wherein peak intensities are used instead of the peak areas.

6. A method of oxygen and/or ozone deterioration analysis, comprising:

subjecting a polymer material containing at least two diene polymers to oxygen and/or ozone deterioration;

irradiating the polymer material containing at least two diene polymers with high intensity x-rays at multiple different wavelengths in sequence in the energy range of 500 to 600 eV; and measuring x-ray absorption correspondingly for each energy irradiation in sequence in a micro area of the polymer material while varying the energy of the x-rays, to analyze deterioration of each diene polymer, wherein the method comprises:

performing waveform separation of an x-ray absorption spectrum of each diene polymer around the oxygen K-shell absorption edge obtained by scanning over a range of high intensity x-ray energies of 500 to 600 eV; and calculating contribution rates of oxygen deterioration and ozone deterioration of each diene polymer according to Equations 2-3, wherein the oxygen deterioration corresponds to a peak on the low energy side with a peak top energy in the range of at least 532 eV but lower than 532.7 eV, and the ozone deterioration corresponds to a peak on the high energy side with a peak top energy in the range of at least 532.7 eV but not higher than 534 eV:

[Peak area of oxygen deterioration of diene polymer $Ai$]/[(Peak area of ozone deterioration of diene polymer $Ai$)+(Peak area of oxygen deterioration of diene polymer $Ai$)]×100=Contribution rate (%) of oxygen deterioration of diene polymer $Ai$, and

[Peak area of ozone deterioration of diene polymer $Ai$]/[(Peak area of ozone deterioration of diene polymer $Ai$)+(Peak area of oxygen deterioration of diene polymer $Ai$)]×100=Contribution rate (%) of ozone deterioration of diene polymer $Ai$, (Equations 2-3)

wherein $Ai$ represents each diene polymer contained in the polymer material.

7. The method according to claim 6, wherein peak intensities are used instead of the peak areas.

8. A method of oxygen and/or ozone deterioration analysis, comprising:

subjecting a polymer material containing at least two diene polymers to oxygen and/or ozone deterioration;

irradiating the polymer material containing at least two diene polymers with high intensity x-rays at multiple different wavelengths in sequence in the energy range of 260 to 400 eV; and measuring x-ray absorption correspondingly for each energy irradiation in sequence in a micro area of the polymer material while varying the energy of the x-rays, to analyze deterioration of each diene polymer, wherein the method comprises:

determining a normalization constant γ using Equation 2-4 from an x-ray absorption spectrum of each diene polymer after deterioration around the carbon K-shell absorption edge; and correcting a total area of an x-ray absorption spectrum of each diene polymer around the oxygen K-shell absorption edge using Equation 2-5 with the normalization constant γ to determine the amount of oxygen and ozone bonded to each diene polymer:

[Total area of x-ray absorption spectrum of diene polymer $Ai$ around carbon K-shell absorption edge]×$\gamma_{Ai}$=1, (Equation 2-4)

wherein $Ai$ represents each diene polymer contained in the polymer material; and

[Total area of x-ray absorption spectrum of diene polymer $Ai$ around oxygen K-shell absorption edge]×$\gamma_{Ai}$=Amount (index) of oxygen and ozone bonded to diene polymer $Ai$, (Equation 2-5)

wherein $Ai$ represents each diene polymer contained in the polymer material.

9. A method of oxygen and/or ozone deterioration analysis, comprising:

subjecting a sulfur cross-linked polymer material to oxygen and/or ozone deterioration;

irradiating the sulfur cross-linked polymer material with x-rays at multiple different wavelengths in sequence in the energy range of 260 to 400 eV, and measuring x-ray absorption correspondingly for each energy irradiation in sequence while varying the energy of the x-rays, to determine deterioration of polymers;

irradiating the sulfur cross-linked polymer material with constant energy x-rays, and measuring excited and emitted photoelectrons to determine deterioration of sulfur crosslinks; and determining a deterioration ratio between polymers and sulfur crosslinks from the deterioration of polymers and the deterioration of sulfur crosslinks, wherein the method comprises:

calculating normalization constants α and β using Equations 3-1 from x-ray absorption spectra obtained by scanning over a range of x-ray energies around the carbon K-shell absorption edge within the range of 260 to 400 eV;

performing waveform separation of the x-ray absorption spectra around the carbon K-shell absorption edge corrected with the normalization constants α and β to obtain peak areas attributed to π* transition at around 285 eV; and determining degree (%) of deterioration of polymers using Equation 3-2 with the obtained peak areas:

[Total area of x-ray absorption spectrum over measurement range of sample before deterioration]×α=1, and

[Total area of x-ray absorption spectrum over measurement range of sample after deterioration]×β=1; and (Equations 3-1)

[1−[(π*peak area after deterioration)×β]/[(π*peak area before deterioration)×α]]×100=Degree (%) of deterioration of polymers. (Equation 3-2)

10. A method of oxygen and/or ozone deterioration analysis, comprising:

subjecting a sulfur cross-linked polymer material to oxygen and/or ozone deterioration;

irradiating the sulfur cross-linked polymer material with x-rays at multiple different wavelengths in sequence in the energy range of 260 to 400 eV, and measuring x-ray absorption correspondingly for each energy irradiation in sequence while varying the energy of the x-rays, to determine deterioration of polymers;

irradiating the sulfur cross-linked polymer material with constant energy x-rays, and measuring excited and emitted photoelectrons to determine deterioration of sulfur crosslinks; and determining a deterioration ratio between polymers and sulfur crosslinks from the deterioration of polymers and the deterioration of sulfur crosslinks, wherein the method comprises:
dispersing the photoelectrons excited and emitted by irradiation with the constant energy x-rays;
measuring S2p photoelectron intensity to obtain an x-ray photoelectron spectrum;
performing waveform separation of the spectrum to obtain a peak area attributed to sulfur oxides; and
determining degree (%) of deterioration of sulfur crosslinks using Equation 3-3 with the obtained peak area:

($S2p$ peak area attributed to sulfur oxides)/(Total $S2p$ peak area)×100=Degree (%) of deterioration of sulfur crosslinks. (Equation 3-3)

11. A method of oxygen and/or ozone deterioration analysis, comprising:
subjecting a sulfur cross-linked polymer material to oxygen and/or ozone deterioration;
irradiating the sulfur cross-linked polymer material with x-rays at multiple different wavelengths in sequence in the energy range of 260 to 400 eV, and measuring x-ray absorption correspondingly for each energy irradiation in sequence while varying the energy of the x-rays, to determine deterioration of polymers;
irradiating the sulfur cross-linked polymer material with constant energy x-rays, and measuring excited and emitted photoelectrons to determine deterioration of sulfur crosslinks; and
determining a deterioration ratio between polymers and sulfur crosslinks from the deterioration of polymers and the deterioration of sulfur crosslinks,
wherein the method comprises:
dispersing the photoelectrons excited and emitted by irradiation with the constant energy x-rays;
measuring S1s photoelectron intensity to obtain an x-ray photoelectron spectrum;
performing waveform separation of the spectrum to obtain a peak area attributed to sulfur oxides; and
determining degree (%) of deterioration of sulfur crosslinks using Equation (3-4) with the obtained peak area:

($S1s$ peak area attributed to sulfur oxides)/(Total $S1s$ peak area)×100=Degree (%) of deterioration of sulfur crosslinks. (Equation 3-4)

12. The method according to claim 11, wherein an energy range of the constant energy x-rays used is from 2.5 to 15 keV.

13. The method according to claim 9, wherein peak intensities are used instead of the peak areas.

14. The method according to claim 9, comprising
calculating a contribution ratio of deterioration of polymers and deterioration of sulfur crosslinks according to Equation 3-5:

[Degree (%) of deterioration of polymers]/[Degree (%) of deterioration of sulfur crosslinks]=Contribution ratio of deterioration of polymers and deterioration of sulfur crosslinks. (Equation 3-5)

15. The method according to claim 2, wherein peak intensities are used instead of the peak areas.

16. The method according to claim 10, wherein peak intensities are used instead of the peak areas.

17. The method according to claim 11, wherein peak intensities are used instead of the peak areas.

18. The method according to claim 12, wherein peak intensities are used instead of the peak areas.

19. The method according to claim 10, comprising
calculating a contribution ratio of deterioration of polymers and deterioration of sulfur crosslinks according to Equation 3-5:

[Degree (%) of deterioration of polymers]/[Degree (%) of deterioration of sulfur crosslinks]=Contribution ratio of deterioration of polymers and deterioration of sulfur crosslinks. (Equation 3-5)

20. The method according to claim 11, comprising
calculating a contribution ratio of deterioration of polymers and deterioration of sulfur crosslinks according to Equation 3-5:

[Degree (%) of deterioration of polymers]/[Degree (%) of deterioration of sulfur crosslinks]=Contribution ratio of deterioration of polymers and deterioration of sulfur crosslinks. (Equation 3-5)

* * * * *